United States Patent
Ikeda et al.

(10) Patent No.: US 10,760,066 B2
(45) Date of Patent: Sep. 1, 2020

(54) METHOD FOR KILLING MICROORGANISM

(71) Applicant: Kabushiki Kaisha Yakult Honsha, Tokyo (JP)

(72) Inventors: Masakazu Ikeda, Tokyo (JP); Tadashi Sato, Tokyo (JP); Keiko Kasaha, Tokyo (JP); Masahiko Ito, Tokyo (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 0 days.

(21) Appl. No.: 16/018,888

(22) Filed: Jun. 26, 2018

(65) Prior Publication Data

US 2018/0362948 A1 Dec. 20, 2018

Related U.S. Application Data

(62) Division of application No. 14/119,071, filed as application No. PCT/JP2012/062746 on May 18, 2012, now abandoned.

(30) Foreign Application Priority Data

May 20, 2011 (JP) ................................. 2011-113170
May 20, 2011 (JP) ................................. 2011-113171

(51) Int. Cl.
*C12N 9/38* (2006.01)
*C12N 1/06* (2006.01)

(52) U.S. Cl.
CPC .............. *C12N 9/2471* (2013.01); *C12N 1/06* (2013.01); *C12Y 302/01023* (2013.01)

(58) Field of Classification Search
CPC combination set(s) only.
See application file for complete search history.

(56) References Cited

FOREIGN PATENT DOCUMENTS

| EP | 2 698 428 A1 | 2/2014 |
|---|---|---|
| JP | 5 58714 | 8/1993 |
| JP | 11 169179 | 6/1999 |
| JP | 2002 355028 | 12/2002 |
| JP | 2003 144144 | 5/2003 |
| JP | 2006-223268 A | 8/2006 |
| JP | 2006 262865 | 10/2006 |
| JP | 2008 255296 | 10/2008 |
| WO | WO 2012/141244 A1 | 10/2012 |

OTHER PUBLICATIONS

Akiyama et al. (Production of galactooligosaccharides from lactose using a beta-glucosidase from *Thermus* species Z-1 (Biosci. Biotechnol. Biochem., 65(2), 438-441, 2001), (Year: 2001).*

Miroliaei, M., et al., "Thermal denaturation of yeast alcohol dehydrogenase and protection of secondary and tertiary structural changes by sugars: CD and fluorescence studies", Enzyme and Microbial Technology, vol. 40, pp. 896-901, (2007).
International Search Report dated Aug. 14, 2012 in PCT/JP12/062746 Filed May 18, 2012.
Extended European Search Report dated Dec. 1, 2014 in the corresponding European Application No. 12790316.9.
Takafumi Sakai, et al., "Repeated-batch production of galactooligosaccharides from lactose at high concentration by using alginate-immobilized cells of Sporobolomyces singularis YIT 10047", J. Gen. Appl. Microbiol., vol. 54, XP002552446, Oct. 1, 2008, pp. 285-293.
I.M. Banat, et al., "Isolation of thermotolerant, fermentative yeasts growing at 52 degree and producing ethanol at 45 degree and 50 degree", World Journal of Microbiology and Biotechnology, Rapid Communications of Oxford, vol. 8, XP003022591, Jan. 1, 1992, pp. 259-263.
Tomoyuki Nakagawa, et al. "Cold-active acid beta-galactosidase activity of isolated psychrophilic-basidiomycetous yeast Guehomyces pullulans", Microbiological Research, vol. 161, No. 1, XP028022039, Jan. 1, 2006, pp. 75-79.
Husain Qayyum, "beta Galactosidases and their potential applications: a review", CRC Critical Reviews in Biotechnology, CRC Press, vol. 30, No. 1, XP009153894, Mar. 1, 2010, pp. 41-62.
Chinese Office Action dated Apr. 7, 2015, in Chinese Patent Application No. 201280024214.1.
Yang Xiaomin, et al., Europe PubMed Central, Effect of sugars on the stability of cellulase, Department of Chemical Engineering, Tsinghua University Beijing 100084; China Journal of Tsinghua University (Science and Technology) (2000, 40(2): 51-54).
Mehren et al (Thermal denaturation of yeast alcohol dehydrogenase and protection of secondary and tertiary structural changes by sugars: CD and fluorescence studies Enzyme and Microbial Technology 40 (2007) 896-901.
Ishikawa et al (Identification, cloning, and characterization of a Sporobolomyces singularis beta-galactosidase-like enzyme involved in galacto-oligosaccharide production). Journal of Bioscience and Bioengineering. The Society for Biotechnology, Japan vol. 99, No. 4, 331-339. 2005.

* cited by examiner

*Primary Examiner* — Kagnew H Gebreyesus
(74) *Attorney, Agent, or Firm* — Oblon, McClelland, Maier & Neustadt, L.L.P.

(57) ABSTRACT

Provided is a technique for enabling a liquid of microbial cells having an enzymatic activity to be easily stored and used. The technique is a method for killing a microorganism while maintaining the enzyme titer of a microbial cell liquid, characterized by including adjusting the pH of a liquid of microbial cells having an enzymatic activity, and then performing a heating treatment of the liquid, and also the technique is a method for killing a microorganism while maintaining the enzyme titer of a microbial cell liquid, characterized by including adding a carbohydrate to a liquid of microbial cells having an enzymatic activity, and then performing a heating treatment of the liquid.

10 Claims, 3 Drawing Sheets

METHOD FOR KILLING MICROORGANISM

CROSS REFERENCE TO RELATED APPLICATIONS

The present application is a divisional of U.S. patent application Ser. No. 14/119,071 (now abandoned), which is a 35 U.S.C. § 371 national stage patent application of International patent application PCT/JP2012/062746, filed on May 18, 2012, published as WO/2012/161108 on Nov. 29, 2012, the text of both of which is incorporated by reference, and claims the benefit of the filing date of Japanese application nos. 2011-113170, filed on May 20, 2011, and 2011-113171, filed on May 20, 2011, the text of both of which is also incorporated by reference.

TECHNICAL FIELD

The present invention relates to a method for killing a microorganism, more particularly relates to a method for killing a microorganism while maintaining the enzyme titer of a liquid of microbial cells having an enzymatic activity.

BACKGROUND ART

There are many microorganisms that have a useful enzymatic activity, and such microorganisms are widely used in the production of functional food materials such as carbohydrates, amino acids, and phospholipids. Among these, there are known many microorganisms which can be used in the production of carbohydrate materials, particularly oligosaccharides, and for example, it has been reported that a galactooligosaccharide is produced by utilizing the β-galactosidase activity of yeast belonging to the genus *Sporobolomyces singularis* (PTL 1).

Generally speaking, a microorganism is killed by a heating treatment and then stored etc, however, in the case where a microorganism having an enzymatic activity as described above is subjected to a heating treatment, whilst the microorganism is killed, the enzymatic activity is significantly decreased, which is practically useless. Further, as a technique for killing a microorganism while maintaining the enzymatic activity, there has been reported a technique for killing a microorganism while maintaining the enzymatic activity in which a transformed microorganism is treated with a chemical such as an alcohol at 25 to 35° C. (PTL 2). However, this technique has a problem that the use thereof after killing the microorganism is limited because a genetically modified microorganism is used or the alcohol or the like used in the treatment for killing the microorganism remains.

CITATION LIST

Patent Literature

PTL 1: JP-B-5-58714
PTL 2: JP-A-2002-355028

SUMMARY OF INVENTION

Problems to be Solved by the Invention

Accordingly, an object of the invention is to provide a technique for enabling a liquid of microbial cells having an enzymatic activity to be easily stored and used.

Means for Solving the Problems of the Invention

The inventors of the present invention made intensive studies of the conditions for killing a microorganism by a heating treatment in order to solve the above problems, and as a result, they found that the microorganism can be killed while maintaining the enzyme titer by adjusting the pH before performing the heating treatment for killing the microorganism in a liquid of microbial cells having an enzymatic activity or by allowing a carbohydrate to be present when performing the heating treatment, and thus completed the invention. Further, they found that the microbial cell liquid in which the microorganism has been killed as described above maintains the enzyme titer of the microbial cell liquid before killing the microorganism, and thus completed the invention.

That is, the invention is directed to a method for killing a microorganism while maintaining the enzyme titer of a microbial cell liquid, characterized by including adjusting the pH of a liquid of microbial cells having an enzymatic activity, and then performing a heating treatment of the liquid.

Further, the invention is directed to a killed microbial cell liquid, characterized in that the enzyme titer of the microbial cell liquid before killing the microorganism is maintained.

Still further, the invention is directed to a method for killing a microorganism while maintaining the enzyme titer of a microbial cell liquid, characterized by including adding a carbohydrate to a liquid of microbial cells having an enzymatic activity, and then performing a heating treatment of the liquid.

Yet still further, the invention is directed to a killed microbial cell liquid, characterized in that a carbohydrate is contained, and the enzyme titer of the microbial cell liquid before killing the microorganism is maintained.

Advantages of the Invention

According to the method for killing a microorganism while maintaining the enzyme titer of a microbial cell liquid of the invention, the microorganism can be killed while maintaining the enzyme titer of a liquid of microbial cells having an enzymatic activity. Further, according to this method, the thermal stability of the enzyme can be increased, and the microorganism can be killed while maintaining the enzyme titer under wider temperature conditions. Therefore, the microbial cell liquid after killing the microorganism can be easily stored and used. That is, in the case where the microorganism is alive, some sort of metabolite is produced by the microorganism during storage to deteriorate the quality of the microbial cell liquid, and also the storage stability of the enzyme titer may be affected. Meanwhile, in the case where the microorganism has been killed, such a problem does not arise, and therefore, the killed microbial cell liquid has excellent storage stability with respect to the enzyme titer.

Further, the killed microbial cell liquid of the invention is configured such that the microorganism has been killed in a state where the enzymatic activity is maintained, and therefore can be easily stored and used.

Further, by drying the above-described killed microbial cell liquid to form a dry killed microbial cell powder, it can be stably stored and used for a longer time.

DESCRIPTION OF EMBODIMENTS

Figure 1:
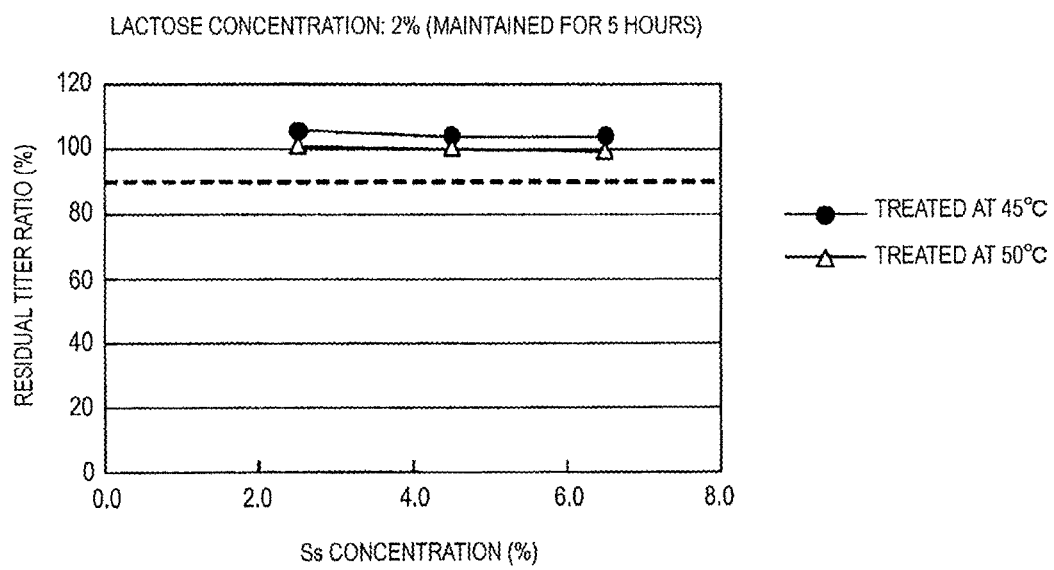
FIG. 1 is a view showing a residual titer ratio after performing a heating treatment by maintaining an Ss concentrate liquid having a lactose concentration of 2 mass/vol % at 45° C. or 50° C. for 5 hours in Example 9.
Figure 2:
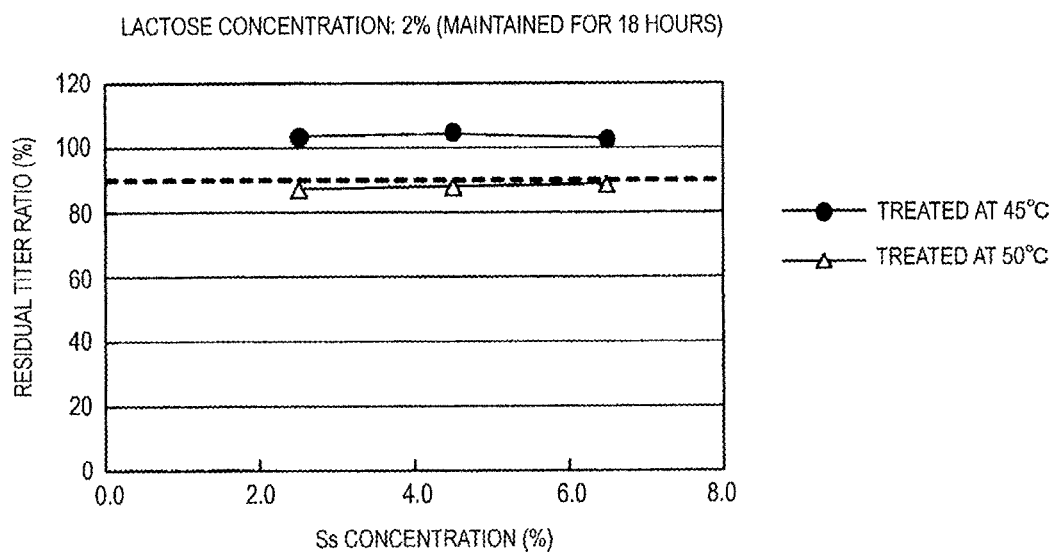
FIG. 2 is a view showing a residual titer ratio after performing a heating treatment by maintaining an Ss concentrate liquid having a lactose concentration of 2 mass/vol % at 45° C. or 50° C. for 18 hours in Example 9.
Figure 3:
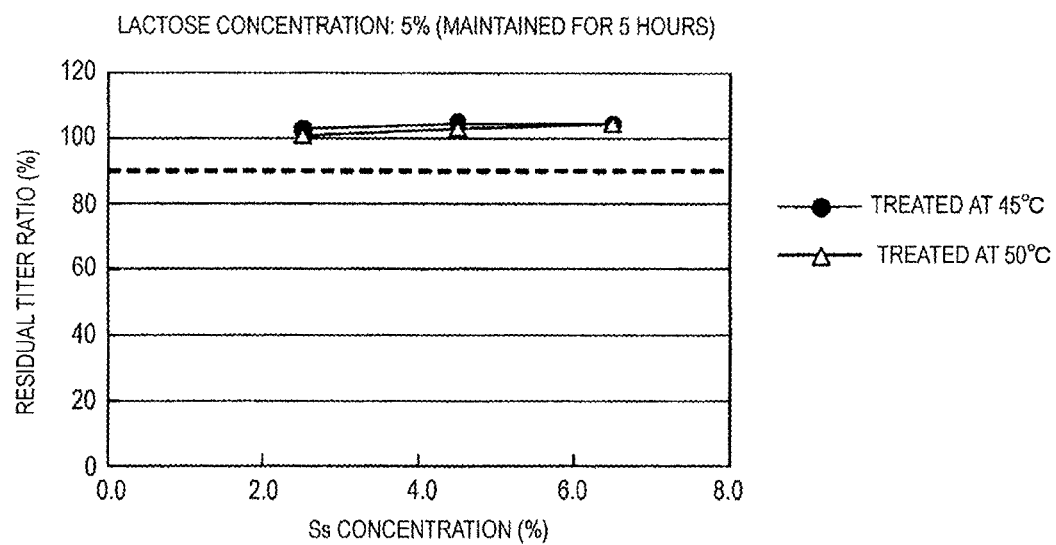
FIG. 3 is a view showing a residual titer ratio after performing a heating treatment by maintaining an Ss concentrate liquid having a lactose concentration of 5 mass/vol % at 45° C. or 50° C. for 5 hours in Example 9.
Figure 4:
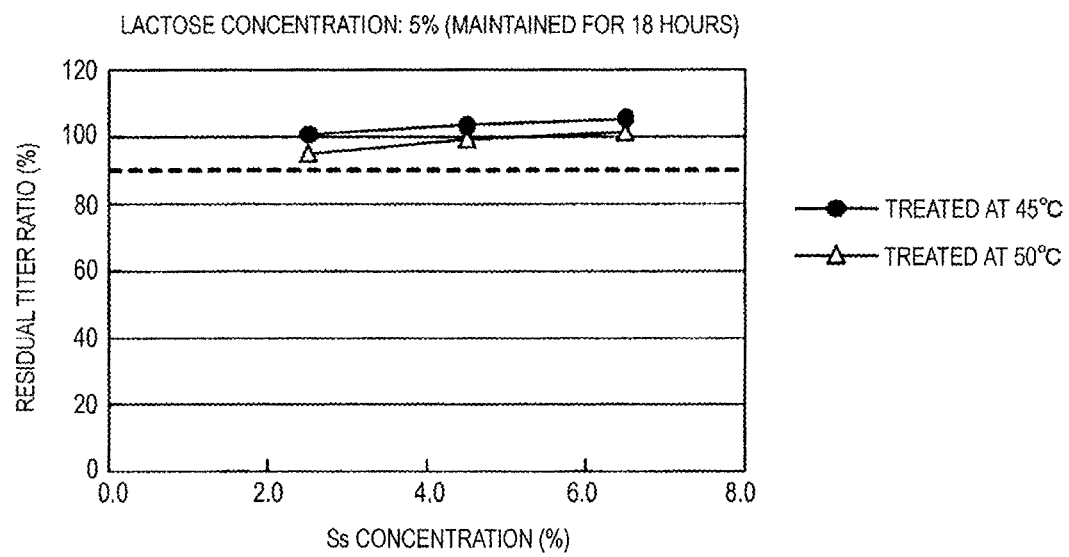
FIG. 4 is a view showing a residual titer ratio after performing a heating treatment by maintaining an Ss concentrate liquid having a lactose concentration of 5 mass/vol % at 45° C. or 50° C. for 18 hours in Example 9.

The method for killing a microorganism while maintaining the enzyme titer of a microbial cell liquid according to the invention (hereinafter referred to as "the present inventive method") can be performed by a method including adjusting the pH of a liquid of microbial cells having an enzymatic activity, and then, performing a heating treatment of the liquid (hereinafter referred to as "the present inventive method 1") or a method including adding a carbohydrate to a liquid of microbial cells having an enzymatic activity, and then performing a heating treatment of the liquid (hereinafter referred to as "the present inventive method 2").

In the present inventive method, the microorganism to be killed is not particularly limited as long as it is a microorganism such as a bacterium, yeast, or a fungus, and an enzyme is bound to cell walls or an enzyme is intracellularly and/or extracellularly produced, that is, it is a microorganism having an enzymatic activity. Examples of such a microorganism having an enzymatic activity include bacteria belonging to the genus *Streptococcus*, the genus *Lactobacillus*, the genus *Bacillus*, the genus *Bifidobacterium*, etc.; and yeast belonging to the genus *Sporobolomyces*, the genus *Bullera*, the genus *Kluyveromyces*, the genus *Lipomyces*, the genus *Candida*, the genus *Cryptococcus*, the genus *Sterigmatomyces*, the genus *Bensingtonia*, the genus *Ballistosporomyces*, the genus *Fellomyces*, the genus *Filobasidium*, the genus *Sirobasidium*, the genus *Tilletiopsis*, the genus *Itersonilia*, the genus *Tilletia*, the genus *Saccharomyces*, the genus *Schizosaccharomyces*, the genus *Hansenula*, the genus *Rhodotorula*, the genus *Debaryomyces*, the genus *Pichia*, and the genus *Torulopsis*. Further, examples of the enzyme include carbohydrate degrading enzymes such as amylase, sucrase, α-galactosidase, β-galactosidase, glucose isomerase, α-glucosidase, β-glucosidase, β-fructofuranosidase, α-mannosidase, β-mannosidase, and xylanase.

Among the above-described microorganisms having an enzymatic activity, a microorganism having β-galactosidase activity is preferred. Examples of such a microorganism include yeast belonging to the genus *Sporobolomyces*, the genus *Bullera*, the genus *Kluyveromyces*, the genus *Lipomyces*, the genus *Candida*, the genus *Cryptococcus*, the genus *Sterigmatomyces*, the genus *Bensingtonia*, the genus *Ballistosporomyces*, the genus *Fellomyces*, the genus *Filobasidium*, the genus *Sirobasidium*, the genus *Tilletiopsis*, the genus *Itersonilia*, the genus *Tilletia*, the genus *Saccharomyces*, the genus *Schizosaccharomyces*, the genus *Hansenula*, the genus *Rhodotorula*, the genus *Debaryomyces*, the genus *Pichia*, and the genus *Torulopsis*; and bacteria belonging to the genus *Streptococcus*, the genus *Lactobacillus*, the genus *Bacillus*, and the genus *Bifidobacterium*.

Further, among the above-described microorganisms having β-galactosidase activity, yeast or a bacterium is preferred, and in particular, yeast is more preferred. Specific examples of the yeast having β-galactosidase activity include particularly *Sporobolomyces singularis*, *Sterigmatomyces elviae*, *Cryptococcus laurentii*, *Rhodotorula lactosa*, *Sirobasidium magnum*, and *Lipomyces lipofer*. Specific examples of the bacterium having β-galactosidase activity include particularly *Streptococcus thermophilus*, *Lactobacillus bulgaricus*, *Streptococcus lactis*, *Lactobacillus salivarius*, *Lactobacillus leichmannii*, *Lactobacillus helveticus*, *Bacillus brevis*, *Bacillus stearothermophilus*, *Bifidobacterium bifidum*, *Bifidobacterium breve*, *Bifidobacterium longum*, and *Bifidobacterium adolescentis*.

As the yeast having β-galactosidase activity which is particularly preferably used, *Sporobolomyces singularis* can be exemplified, and *Sporobolomyces singularis* JCM 5356 (ATCC 24193), which is one of the examples thereof, is available for a fee from RIKEN BioResource Center (2-1 Hirosawa, Wako-shi, Saitama-ken, 351-0198, Japan), ATCC (10801 University Boulevard Manassas, Va., 20110, USA), or the like.

Further, as another example of *Sporobolomyces singularis*, yeast obtained as a β-galactosidase high-producing mutant microorganism by a production method described in JP-A-2003-325166 can be exemplified. Among these, as a specific example of yeast obtained by the steps (a) to (c) in the above-described patent literature using the above-described *Sporobolomyces singularis* JCM 5356 as a parent strain, *Sporobolomyces singularis* ISK-#4D4, ISK-#5A5, and ISK-##2B6 can be exemplified, and these strains were deposited on Apr. 10, 2002 in International Patent Organism Depositary, National Institute of Advanced Industrial Science and Technology (Chuo 6, Higashi 1-1-1, Tsukuba-shi, Ibaraki-ken, 305-8566, Japan) under accession Nos. FERM β-18818, FERM β-18819, and FERM β-18817, respectively.

Among the present inventive methods for killing a microorganism described above, the method including adjusting the pH of a liquid of microbial cells having an enzymatic activity, and then performing a heating treatment of the liquid (the present inventive method 1) will be described. In the implementation of the present inventive method 1, first, a culture solution is obtained by culturing a microorganism having an enzymatic activity in a medium or the like according to a common procedure. This culture solution may be used as the microbial cell liquid as it is, or a liquid obtained by appropriately performing washing or concentration using a centrifuge, a membrane concentration device, or the like may be used as the microbial cell liquid. The solid content in this microbial cell liquid is not particularly limited, and specifically, a solid content of 0.5 to 10% can be exemplified. Incidentally, the "solid content" in this specification refers to a solid content of the cells in the microbial cell liquid, and for example, in the case where medium components are contained in the microbial cell liquid, the solid content derived from the medium components is not included in the "solid content" in this specification.

Subsequently, the pH of this microbial cell liquid is adjusted. The range of the pH is not particularly limited, however, from the viewpoint that the enzyme titer can be maintained higher in a wider temperature range, the range of the pH is preferably from 3.5 to 6.5, more preferably from 4.2 to 6.3, further more preferably from 4.5 to 5.7. A substance to be used for adjusting the pH is not particularly limited, and any of an acid, a base, and a salt can be used. Specifically, hydrochloric acid, acetic acid, sulfuric acid, an aqueous solution of sodium hydroxide, potassium hydroxide, sodium carbonate, or the like, or any of a variety of buffers such as a sodium phosphate buffer can be used as needed, however, from the viewpoint that the titer after the pH adjustment is not decreased, it is preferred to use a carbonate, and it is more preferred to use one or more carbonates selected from the group consisting of sodium carbonate, potassium carbonate, ammonium carbonate, sodium hydrogen carbonate, potassium hydrogen carbonate, and ammonium hydrogen carbonate.

Incidentally, from the viewpoint that the thermal stability of the enzyme is further improved and the enzyme titer can be maintained higher, it is preferred that a carbohydrate is added to the microbial cell liquid before adjusting the pH and/or a carbohydrate is added to the microbial cell liquid after adjusting the pH and before performing the heating treatment. The carbohydrate to be used here is not particularly limited, and any of a monosaccharide, a disaccharide, a tri- or higher oligosaccharide, and a polysaccharide can be used. Examples of the monosaccharide include glucose, galactose, fructose, and mannose, examples of the disaccharide include lactose, lactose isomers, maltose, sucrose, and trehalose, examples of the tri- or higher oligosaccharide include various oligosaccharides such as galactooligosaccharides, maltooligosaccharides, and fructooligosaccharides, and examples of the polysaccharide include dextrins and starch. Among these carbohydrates, from the viewpoints of an effect of maintaining the enzyme titer and cost, at least one carbohydrate selected from the group consisting of lactose, glucose, maltose, a galactooligosaccharide, and a dextrin is preferred, and in particular, it is preferred to use at least one carbohydrate selected from the group consisting of lactose, glucose, maltose, and a galactooligosaccharide. The amount of the carbohydrate to be added to the microbial cell liquid is not particularly limited, however, the lower limit of the addition amount of the carbohydrate is, for example, preferably 0.2 mass/vol % (hereinafter simply expressed in "%") or more, more preferably 0.5% or more, further more preferably 2% or more with respect to the amount of the microbial cell liquid. Further, when or how the carbohydrate is added to the microbial cell liquid is not particularly limited, and for example, a method in which a separately prepared concentrated solution of the carbohydrate is added can be exemplified, however, when the amount of a carbohydrate solution to be added to the microbial cell liquid is too large, a problem may arise in some cases that the concentration of the microbial cells in the microbial cell liquid is decreased, and therefore, the enzyme titer per unit weight of the microbial cell liquid is decreased. Accordingly, the upper limit of the addition amount of the carbohydrate is preferably 30% or less, more preferably 15% or less, further more preferably 10% or less. In view of this, the amount of the carbohydrate to be added to the microbial cell liquid is preferably from 0.2 to 30%, more preferably from 0.5 to 15%, further more preferably from 0.5 to 10%, particularly preferably from 2 to 10%.

In the case where the carbohydrate to be added to the microbial cell liquid can be a substrate for the enzyme (for example, in the case where lactose is added to a liquid of microbial cells having β-galactosidase activity), there may be cases where part or most of the carbohydrate is subjected to an enzymatic reaction during a period from when the carbohydrate is added to when the heating treatment is completed, however, the effect of the addition of the carbohydrate is exhibited regardless of the degree of reaction (the degree of degradation or the degree of polymerization), and therefore, there is no problem at all from the viewpoint of stabilization of the enzyme titer. For example, after the carbohydrate is added, even if the microbial cell liquid is kept as it is, or is subjected to a cooling treatment or a heating treatment, there is no problem at all from the viewpoint of stabilization of the enzyme titer. In addition, in such a case, another carbohydrate produced by subjecting the added carbohydrate to the enzymatic reaction is contained in the microbial cell liquid in some cases, however, even if such a carbohydrate is present, there is no problem at all from the viewpoint of stabilization of the enzyme titer. Examples of the carbohydrate to be produced by subjecting the carbohydrate added to the microbial cell liquid to the enzymatic reaction include monosaccharides, disaccharides, tri- or higher oligosaccharides, and polysaccharides, and examples of the monosaccharide include glucose, galactose, fructose, and mannose, examples of the disaccharide include lactose, lactose isomers, maltose, sucrose, and trehalose, examples of the tri- or higher oligosaccharide include various oligosaccharides such as galactooligosaccharides and fructooligosaccharides, and examples of the polysaccharide include dextrins and starch. Specifically, in the case where the carbohydrate to be added to the liquid of the microbial cells having a carbohydrate degrading enzyme (for example, β-galactosidase) activity is lactose, since lactose is subjected to the enzymatic reaction, as the carbohydrate contained in the microbial cell liquid, glucose, galactose, lactose, a lactose isomer, and a galactooligosaccharide can be exemplified; as the carbohydrate contained in the microbial cell liquid in the case where the carbohydrate to be added is maltose, glucose, maltose, and a maltooligosaccharide can be exemplified; and as the carbohydrate contained in the microbial cell liquid in the case where the carbohydrate to be added is a dextrin, glucose, maltose, a maltooligosaccharide, and a dextrin can be exemplified. Since it is preferred to use at least one carbohydrate selected from the group consisting of lactose, glucose, maltose, a galactooligosaccharide, and a dextrin as the carbohydrate to be added to the microbial cell liquid, it is preferred that in the microbial cell liquid to which such a carbohydrate was added, such a carbohydrate and a carbohydrate produced by subjecting such a carbohydrate to the enzymatic reaction are contained, specifically, at least one carbohydrate selected from the group consisting of lactose, glucose, galactose, a lactose isomer, a galactooligosaccharide, maltose, a maltooligosaccharide, and a dextrin is contained. Further, since it is more preferred to use at least one carbohydrate selected from the group consisting of lactose, glucose, maltose, and a galactooligosaccharide as the carbohydrate to be added to the microbial cell liquid, it is more preferred that in the microbial cell liquid, at least one carbohydrate selected from the group consisting of lactose, glucose, galactose, a lactose isomer, a galactooligosaccharide, maltose, and a maltooligosaccharide is contained.

After adjusting the pH as described above, a heating treatment is performed. The heating treatment method is not particularly limited, and a method using a continuous plate heat exchanger, a method of heating a tank containing the microbial cell liquid by heating steam or hot water in a batchwise process, or the like can be applied, however, in order to control the temperature so as to prevent the inactivation of the enzyme as much as possible, a method of heating a tank containing the microbial cell liquid by heating steam or hot water in a batchwise process is preferred. The heating treatment in a batchwise process is not particularly limited as long as the conditions for the heating treatment can kill the microorganism while maintaining the enzyme titer, however, it is performed at preferably 40 to 50° C., more preferably 40 to 48° C., further more preferably 40 to 46° C. Further, in the case where a carbohydrate is added to the microbial cell liquid before adjusting the pH and/or a carbohydrate is added to the microbial cell liquid after adjusting the pH and before performing the heating treatment in a batchwise process, the heating treatment is performed at preferably 40 to 60° C., more preferably 40 to 55° C., further more preferably 40 to 50° C. Further, the heating time is also not particularly limited, but is preferably 1 hour or more, more preferably 6 hours or more. However, if the heating time is too long, the enzyme titer is decreased in some cases, and therefore, the heating time is preferably 24 hours or less, more preferably 20 hours or less, further more preferably 18 hours or less. In view of this, the heating time is preferably from 1 to 24 hours, more preferably from 1 to 20 hours, further more preferably from 1 to 18 hours, still further more preferably from 6 to 24 hours, yet still further more preferably from 6 to 20 hours, particularly preferably from 6 to 18 hours. Further, in the case where a carbohydrate is added before performing the heating treatment, the heating time is preferably from 1 to 24 hours, more preferably from 4 to 20 hours, further more preferably from 5 to 18 hours. Incidentally, the phrase "killing a microorganism" in the present inventive method 1 refers to the reduction of the live microbial cells by the heating treatment to 1000 cfu/mL or less, and it is desirable to reduce the live microbial cells to preferably 100 cfu/mL or less, more preferably 10 cfu/mL or less.

By performing the heating treatment as described above, the microorganism in the microbial cell liquid is killed while maintaining the enzyme titer of the microbial cell liquid. Here, the phrase "maintaining the enzyme titer" refers to that the enzyme titer after performing the heating treatment (after killing the microorganism) is 80% or more, preferably 90% or more, more preferably 95% or more of the enzyme titer before performing the heating treatment (before killing the microorganism).

The microbial cell liquid after the heating treatment (a killed microbial cell liquid) can be stored for a long time under low-temperature conditions of 25° C. or lower, preferably from 0 to 5° C. Then, the microbial cell liquid after the heating treatment can be used in various applications using the enzymatic activity.

In addition, the microbial cell liquid after the heating treatment can be further dried by a known drying method such as spray drying or lyophilization and formed into a killed microbial cell dry powder. At this time, in order to prevent a decrease in enzyme titer due to the drying step or storage after drying, it is also possible to add a carbohydrate to the microbial cell liquid after the heating treatment. The carbohydrate to be used is not particularly limited, and any of a monosaccharide, a disaccharide, a tri- or higher oligosaccharide, and a polysaccharide can be used. Examples of the monosaccharide include glucose, galactose, fructose, and mannose, examples of the disaccharide include lactose, lactose isomers, maltose, sucrose, and trehalose, examples of the tri- or higher oligosaccharide include various oligosaccharides such as galactooligosaccharides, maltooligosaccharides, and fructooligosaccharides, and examples of the polysaccharide include dextrins and starch. Among these carbohydrates, from the viewpoints of an effect of maintaining the enzyme titer, ease of drying, and cost, it is preferred to use at least one carbohydrate selected from the group consisting of lactose, maltose, and a dextrin, and in particular, it is preferred to use lactose and/or maltose, and it is more preferred to use lactose. The amount of the carbohydrate to be added is not particularly limited, and the lower limit of the addition amount of the carbohydrate is, for example, preferably 0.1% or more, more preferably 0.5% or more, further more preferably 1% or more with respect to the amount of the microbial cell liquid. On the other hand, if the amount of the carbohydrate to be added to the microbial cell liquid is too large, the enzyme titer per unit weight of the dry microbial cell powder is decreased when the microbial cell liquid is formed into a dry powder, and therefore, the upper limit of the addition amount of the carbohydrate is preferably 30% or less, more preferably 15% or less, further more preferably 10% or less, still further more preferably 5% or less, yet still furthermore preferably 3% or less. In view of this, the amount of the carbohydrate to be added to the microbial cell liquid is preferably from 0.1 to 30%, more preferably from 0.5 to 15%, further more preferably from 0.5 to 10%, still further more preferably from 1 to 10%, yet still further more preferably from 1 to 5%, particularly preferably from 1 to 3% with respect to the amount of the microbial cell liquid. The method for adding the carbohydrate is not particularly limited, however, for example, a method in which a separately prepared concentrated solution of the carbohydrate is added can be exemplified. The degree of drying is not particularly limited, however, for example, the drying is performed until the water content in the dry powder is reduced to about 10% or less. By performing this drying, longer time storage as compared with the case of a liquid, for example, 1 year or longer storage can be achieved while maintaining the enzyme titer at 80% or more of the enzyme titer immediately after drying. Further, the dry killed microbial cell powder can be used in various applications using the enzymatic activity.

As for the conditions for the above-described spray drying, the inlet and outlet temperatures of a drying chamber may be in a range in which the enzyme is not significantly inactivated, and further, the rotation speed of an atomizer, the feeding amount of a stock solution, etc. hardly affect the final enzyme titer, although a dry microbial cell powder having slightly different properties as a product is obtained depending on such conditions, and therefore, it is not necessary to pay much attention to such conditions. Specifically, the inlet temperature of a drying chamber can be, for example, from 70° C. to 200° C., preferably from 110° C. to 180° C., and the outlet temperature of a drying chamber can be, for example, from 50° C. to 120° C., preferably from 70° C. to 90° C. Further, the rotation speed of an atomizer can be, for example, from 10, 000 to 30,000 rpm, and the feeding amount of a stock solution can be, for example, from 0.2 to 200 kg/hour. The spray drying can also be performed using a spraying system such as a two-fluid nozzle other than an atomizer. Incidentally, from the viewpoint that continuous production can be performed industrially, it is preferred to use a spray drying method.

The thus obtained microbial cell liquid after the heating treatment and dry killed microbial cell powder can also be incorporated alone or in combination with each other to form an enzyme composition. It is also possible to add a diluent, an excipient, a surfactant, a preservative, or the like to this enzyme composition within a range that does not affect the enzymatic activity. Further, also this enzyme composition can be used in various applications using the enzymatic activity.

Next, among the above-described present inventive methods for killing a microorganism, a method including adding a carbohydrate to a liquid of microbial cells having an enzymatic activity, and then performing a heating treatment of the liquid (the present inventive method 2) will be described. In the implementation of the present inventive method 2, first, a culture solution is obtained by culturing a microorganism having an enzymatic activity in a medium or the like according to a common procedure. This culture solution may be used as the microbial cell liquid as it is, or a liquid obtained by appropriately performing washing or concentration using a centrifuge, a membrane concentration device, or the like may be used as the liquid of microbial cells having an enzymatic activity. The solid content in this microbial cell liquid is not particularly limited, and specifically, a solid content of 0.5 to 10% can be exemplified. As described above, the "solid content" in this specification refers to a solid content of the cells in the microbial cell liquid, and for example, in the case where medium components are contained in the microbial cell liquid, the solid content derived from the medium components is not included in the "solid content" in this specification.

Subsequently, a carbohydrate is added to this microbial cell liquid. The carbohydrate to be used here is not particularly limited, and any of a monosaccharide, a disaccharide, a tri- or higher oligosaccharide, and a polysaccharide can be used. Examples of the monosaccharide include glucose, galactose, fructose, and mannose, examples of the disaccharide include lactose, lactose isomers, maltose, sucrose, and trehalose, examples of the tri- or higher oligosaccharide include various oligosaccharides such as galactooligosaccharides, maltooligosaccharides, and fructooligosaccharides, and examples of the polysaccharide include dextrins and starch. Among these carbohydrates, from the viewpoints of an effect of maintaining the enzyme titer and cost, at least one carbohydrate selected from the group consisting of lactose, glucose, maltose, a galactooligosaccharide, and a dextrin is preferred, and in particular, it is preferred to use at least one carbohydrate selected from the group consisting of lactose, glucose, maltose, and a galactooligosaccharide. The amount of the carbohydrate to be added to the microbial cell liquid is not particularly limited, however, the lower limit of the addition amount of the carbohydrate is, for example, preferably 0.2% or more, more preferably 0.5% or more, further more preferably 2% or more with respect to the amount of the microbial cell liquid. Further, when or how the carbohydrate is added to the microbial cell liquid is not particularly limited, and for example, a method in which a separately prepared concentrated solution of the carbohydrate is added can be exemplified, however, when the amount of a carbohydrate solution to be added to the microbial cell liquid is too large, a problem may arise in some cases that the concentration of the microbial cells in the microbial cell liquid is decreased, and therefore, the enzyme titer per unit weight of the microbial cell liquid is decreased. Accordingly, the upper limit of the addition amount of the carbohydrate is preferably 30% or less, more preferably 15% or less, further more preferably 10% or less. In view of this, the amount of the carbohydrate to be added to the microbial cell liquid is preferably from 0.2 to 30%, more preferably from 0.5 to 15%, further more preferably from 0.5 to 10%, particularly preferably from 2 to 10%.

After adding a carbohydrate to the microbial cell liquid as described above, a heating treatment is performed. The heating treatment method is not particularly limited, and a method using a continuous plate heat exchanger, a method of heating a tank containing the microbial cell liquid by heating steam or hot water in a batchwise process, or the like can be applied, however, in order to control the temperature so as to prevent the inactivation of the enzyme as much as possible, a method of heating a tank containing the microbial cell liquid by heating steam or hot water in a batchwise process is preferred. The heating treatment in a batchwise process is not particularly limited as long as the conditions for the heating treatment can kill the microorganism while maintaining the enzyme titer, however, it is performed at preferably 40 to 60° C., more preferably 40 to 55° C., further more preferably 40 to 50° C. Further, the heating time is also not particularly limited, but is preferably 1 hour or longer, more preferably 4 hours or longer, further more preferably 5 hours or longer. However, if the heating time is too long, the enzyme titer may be decreased, and therefore, the heating time is preferably 24 hours or shorter, more preferably 20 hours or shorter, further more preferably 18 hours or shorter. In view of this, the heating time is preferably from 1 to 24 hours, more preferably from 4 to 20 hours, furthermore preferably from 5 to 18 hours. The phrase "killing a microorganism" in the present inventive method 2 refers to the reduction of the live microbial cells by the heating treatment to 1000 cfu/mL or less, and it is desirable to reduce the live microbial cells to preferably 100 cfu/mL or less, more preferably 10 cfu/mL or less.

By performing the heating treatment as described above, the microorganism in the microbial cell liquid is killed while maintaining the enzyme titer of the microbial cell liquid. Here, the phrase "maintaining the enzyme titer" refers to that the enzyme titer after performing the heating treatment (after killing the microorganism) is 80% or more, preferably 90% or more, more preferably 95% or more of the enzyme titer before performing the heating treatment (before killing the microorganism).

In the case where the carbohydrate to be added to the microbial cell liquid can be a substrate for the enzyme (for example, in the case where lactose is added to a liquid of microbial cells having β-galactosidase activity), there may be cases where part or most of the carbohydrate is subjected to an enzymatic reaction during a period from when the carbohydrate is added to when the heating treatment is completed, however, the effect of the addition of the carbohydrate is exhibited regardless of the degree of reaction (the degree of degradation or the degree of polymerization), and therefore, there is no problem at all from the viewpoint of stabilization of the enzyme titer. For example, after the carbohydrate is added, even if the microbial cell liquid is kept as it is, or is subjected to a cooling treatment or a heating treatment, there is no problem at all from the viewpoint of stabilization of the enzyme titer. In addition, in such a case, another carbohydrate produced by subjecting the added carbohydrate to the enzymatic reaction is contained in the microbial cell liquid, however, even if such a carbohydrate is present, there is no problem at all from the viewpoint of stabilization of the enzyme titer. Examples of the carbohydrate to be contained in the microbial cell liquid include monosaccharides, disaccharides, tri- or higher oligosaccharides, and polysaccharides, and examples of the monosaccharide include glucose, galactose, fructose, and mannose, examples of the disaccharide include lactose, lactose isomers, maltose, sucrose, and trehalose, examples of the tri- or higher oligosaccharide include various oligosaccharides such as galactooligosaccharides and fructooligosaccharides, and examples of the polysaccharide include dextrins and starch. Specifically, in the case where the carbohydrate to be added to the liquid of the microbial cells having a carbohydrate degrading enzyme (for example, β-galactosidase) activity is lactose, since lactose is subjected to the enzymatic reaction, as the carbohydrate contained in the microbial cell liquid, glucose, galactose, lactose, a lactose isomer, and a galactooligosaccharide can be exemplified; as the carbohydrate contained in the microbial cell liquid in the case where the carbohydrate to be added is maltose, glucose, maltose, and a maltooligosaccharide can be exemplified; and as the carbohydrate contained in the microbial cell liquid in the case where the carbohydrate to be added is a dextrin, glucose, maltose, a maltooligosaccharide, and a dextrin can be exemplified. Since it is preferred to use at least one carbohydrate selected from the group consisting of lactose, glucose, maltose, a galactooligosaccharide, and a dextrin as the carbohydrate to be added to the microbial cell liquid, it is preferred that in the microbial cell liquid to which such a carbohydrate was added, such a carbohydrate and a carbohydrate produced by subjecting such a carbohydrate to the enzymatic reaction are contained, specifically, at least one carbohydrate selected from the group consisting of lactose, glucose, galactose, a lactose isomer, a galactooligosaccharide, maltose, a maltooligosaccharide, and a dextrin is contained. Further, since it is more preferred to use at least one carbohydrate selected from the group consisting of lactose, glucose, maltose, and a galactooligosaccharide as the carbohydrate to be added to the microbial cell liquid, it is more preferred that in the microbial cell liquid, at least one carbohydrate selected from the group consisting of lactose, glucose, galactose, a lactose isomer, a galactooligosaccharide, maltose, and a maltooligosaccharide is contained.

The microbial cell liquid after the heating treatment (a killed microbial cell liquid) can be stored for a long time under low-temperature conditions of 25° C. or lower, preferably from 0 to 5° C. Then, the microbial cell liquid after the heating treatment can be used in various applications using the enzymatic activity.

In addition, the microbial cell liquid after the heating treatment can be further dried by a known drying method such as spray drying or lyophilization and formed into a dry killed microbial cell powder. The degree of drying is not particularly limited, however, for example, the drying is performed until the water content in the dry powder is reduced to about 10% or less. By performing this drying, longer time storage as compared with the case of a liquid, for example, 1 year or more storage can be achieved while maintaining the enzyme titer at 80% or more of the enzyme titer immediately after drying. Further, the dry killed microbial cell powder can be used in various applications using the enzymatic activity.

As for the conditions for the above-described spray drying, the inlet and outlet temperatures of a drying chamber may be in a range in which the enzyme is not significantly inactivated, and further, the rotation speed of an atomizer, the feeding amount of a stock solution, etc. hardly affect the final enzyme titer, although a dry microbial cell powder having slightly different properties as a product is obtained depending on such conditions, and therefore, it is not necessary to pay much attention to such conditions. Specifically, the inlet temperature of a drying chamber can be, for example, from 70° C. to 200° C., preferably from 110° C. to 180° C., and the outlet temperature of a drying chamber can be, for example, from 50° C. to 120° C., preferably from 70° C. to 90° C. Further, the rotation speed of an atomizer can be, for example, from 10,000 to 30,000 rpm, and the feeding amount of a stock solution can be, for example, from 0.2 to 200 kg/hour. The spray drying can also be performed using a spraying system such as a two-fluid nozzle other than an atomizer. Incidentally, from the viewpoint that continuous production can be performed industrially, it is preferred to use a spray drying method.

The thus obtained microbial cell liquid after the heating treatment and dry killed microbial cell powder can also be incorporated alone or in combination with each other to form an enzyme composition. It is also possible to add a diluent, an excipient, a surfactant, a preservative, or the like to this enzyme composition within a range that does not affect the enzymatic activity. Further, also this enzyme composition can be used in various applications using the enzymatic activity.

EXAMPLES

Next, the invention will be more specifically described with reference to Examples, however, the invention is by no means limited to these Examples. Incidentally, in the following Examples, the β-galactosidase titer, the solid content, the residual water content in the dry microbial cell powder, a particle size distribution, the live cell count of *Sporobolomyces singularis*, and the sugar composition were measured or analyzed by the following methods.

(1) Method for Measurement of β-Galactosidase Titer (a) Preparation of Test Liquid About 2.5 g to about 6.0 g of a microbial cell liquid was accurately weighed in a 50-mL volumetric flask, and brought to a constant volume with a 50 mM sodium phosphate-citric acid buffer solution (pH 4.0) (hereinafter referred to as "buffer solution"), and then, sufficiently dissolved or suspended therein, whereby a test liquid was prepared. Further, in the case where the microbial cell liquid contained a carbohydrate (lactose), about 2.5 g of the microbial cell liquid was accurately weighed in a 50-mL centrifugal tube, and washing was performed by suspending the liquid in the buffer solution, followed by centrifugation (20,000 G, 15 mins), whereby the carbohydrate was removed. After this washing procedure was performed 3 times, the washed material was transferred to a 50-mL measuring flask, brought to a constant volume with the buffer solution, and well suspended therein, whereby a test liquid was prepared. Further, in the case where a test sample was a dry microbial cell powder (hereinafter referred to as "dry product"), about 150 to 350 mg of the dry product was washed in the same manner as described above, and thereafter a test sample was prepared.

(b) Measurement

In a 100-mL volumetric flask, 0.3766 g of o-nitrophenyl-β-D-galactopyranoside (ONPG) was weighed, dissolved in the buffer solution and brought to a constant volume, whereby a 12.5 mM ONPG solution was prepared. In a test tube, 0.8 mL of this ONPG solution was placed, and the test tube was maintained in a thermoregulated water bath at 30° C. for 5 minutes. Thereto, 0.2 mL of the test liquid was added and mixed well, and a reaction was allowed to proceed at 30° C. for 10 minutes. Then, 4 mL of a 0.25 M sodium carbonate solution was added to stop the reaction (a test system). Separately, in a test tube, 0.8 mL of the ONPG solution and 4 mL of a 0.25 M sodium carbonate solution were placed, and further 0.2 mL of the test liquid was added thereto and mixed well (a blank system). Each of the test system and the blank system was centrifuged (2,000 G, 10 mins, 15 to 20° C.), and the absorbance of the resulting supernatant was measured at a wavelength of 420 nm, and then, the number of units was calculated according to the following formula. The amount of the enzyme required for releasing 1 μmol of o-nitrophenol (ONP) in 1 minute under the above-described reaction conditions was determined as 1 U.

$$\text{Activity value}^* = \frac{A_1 - A_2}{0.91} \times \frac{1}{0.2} \times \frac{1}{10} \times B \quad \text{[Math. 1]}$$

$A_1$: absorbance of test liquid $A_2$: absorbance of blank $B$: dilution ratio

*: U/g (2) Solid Content 5 to 10 g or 5 to 10 mL of a microbial cell liquid before and after performing a treatment of killing a microorganism was accurately weighed on an aluminum dish, followed by drying at 105° C. for 16 hours. From the weights of the microbial cell liquid before and after drying by this procedure, the solid content (mass %) was calculated. Further, in spray drying, the solid content in a stock solution to be dried and in a dry product to be used when the β-galactosidase titer per solid content is calculated were also obtained under the same conditions. Incidentally, when the microbial cell liquid was a culture solution (when medium components were contained), the microbial cell liquid was accurately weighed in a centrifugal tube, and washing was performed by centrifugation to remove the medium components, and then, the entire amount of the washed microbial cells were transferred onto an aluminum dish, and the microbial cells were dried in the same manner as described above, and then, the solid content was calculated.

(3) Residual Water Content

The residual water content in the dry product obtained by spray drying was measured using an infrared aquameter manufactured by Kett Electric Laboratory under the conditions of 105° C. for 15 minutes.

(4) Particle Size Distribution

The particle size distribution of the dry product was measured by a dry process using a laser diffraction particle size distribution analyzer (HELOS & RODOS system) manufactured by Sympatec, Inc.

(5) Live Cell Count of *Sporobolomyces singularis*

Lactose (2.50), yeast extract (0.5%), monopotassium phosphate (0.1%), magnesium sulfate (0.05%), and agar (1.5%) were dissolved, and the pH of the resulting solution was adjusted to 5.0 with 2 N hydrochloric acid. Then, the solution was sterilized by autoclaving (121° C., 10 mins), and a flat plate (φ 90 mm) was prepared. On this plate, 100 μL of a sample dissolved and diluted with physiological saline was plated, and cultured at 25° C. for about 1 week. The resulting colonies were counted and the obtained value was determined as the live cell count of *Sporobolomyces singularis*.

(6) Analysis of Sugar Composition

The sugar composition was analyzed using HPLC under the following conditions.

[HPLC Conditions]

Column: Shodex SUGAR KS-802 (Showa Denko K.K.)
Solvent: pure water
Flow rate: 0.5 mL/min
Temperature: 80° C.
Detector: Differential refractometer Example 1

Killing of Microorganism:

(1) Culturing

*Sporobolomyces singularis* YIT 10047 (ISK-##2B6, hereinafter referred to as "Ss") was aerobically cultured at 27° C. for 4 days in a medium (pH 5) containing glucose (5%), yeast extract (1.0%), monopotassium phosphate (0.1%), and magnesium sulfate (0.05%). This culture solution was centrifuged (10000 G, 30 mins) to obtain wet cells, and sterilized tap water was added thereto and the wet cells were well suspended therein. The resulting suspension was centrifuged under the same conditions, and the obtained wet cells were suspended in a small amount of tap water such that the solid content was about 5%, and the thus obtained suspension was used as an Ss concentrate liquid.

(2) Killing of Microorganism <Examination of pH and Heating Temperature>

The pH of the Ss concentrate liquid (solid content: 5.0%) obtained in the above (1) was adjusted stepwise from 3.5 to 6.3 with a 5 N sodium hydroxide solution. The thus obtained liquids and the Ss concentrate liquid with an unadjusted pH of 3.1 were subjected to a heating treatment by maintaining the liquids at 35° C., 40° C., 45° C., 50° C., or 55° C. for 18 hours. The results of the live cell count of Ss before and after the heating treatment and the ratio of the β-galactosidase titer after the heating treatment to the β-galactosidase titer before the heating treatment (residual titer ratio) are shown in Table 1.

TABLE 1

| | Before heating | | | | | | | | | | |
|---|---|---|---|---|---|---|---|---|---|---|---|
| | | 35° C. | | 40° C. | | 45° C. | | 50° C. | | 55° C. | |
| | Live cell count (cfu/mL) | Residual titer ratio (%) | Live cell count (cfu/mL) | Residual titer ratio (%) | Live cell count (cfu/mL) | Residual titer ratio (%) | Live cell count (cfu/mL) | Residual titer ratio (%) | Live cell count (cfu/mL) | Residual titer ratio (%) | Live cell count (cfu/mL) |
| pH 3.1 (unadjusted) | 5.2E+09 | 97.6 | 5.0E+01 | 92.2 | <10 | 68.5 | <10 | 22.6 | <10 | — | — |
| pH 3.5 | 3.7E+09 | 99.4 | <10 | 102.6 | <10 | 89.4 | <10 | 42.6 | <10 | — | — |
| pH 4.0 | 1.2E+10 | — | — | 96.3 | <10 | 82.9 | <10 | 25.8 | <10 | 0.9 | <10 |
| pH 4.2 | 3.9E+09 | 97.6 | 1.7E+03 | 102.5 | <10 | 97.5 | <10 | 63.3 | <10 | — | — |
| pH 4.7 | 4.9E+09 | 97.7 | 4.4E+04 | 100.2 | <10 | 97.5 | <10 | 70.0 | <10 | — | — |
| pH 5.0 | 1.5E+10 | — | — | 99.5 | <10 | 94.8 | <10 | 53.1 | <10 | 1.2 | <10 |
| pH 5.8 | 9.0E+09 | — | — | 101.1 | <10 | 98.3 | <10 | 59.0 | <10 | 2.1 | <10 |
| pH 6.3 | 6.0E+09 | — | — | 97.5 | <10 | 94.1 | <10 | 54.4 | <10 | 1.0 | <10 |

—: not tested

In the case where the heating treatment was performed after adjusting the pH to 3.5 or 4.0, the Ss was killed at a heating temperature of 40 to 45° C., and the residual titer ratio was 80% or more at 45° C., and 90% or more at 40° C. In the case where the pH was adjusted to 3.5, the Ss was killed and the residual titer ratio was 90% or more even at 35° C. In the case where the heating treatment was performed after adjusting the pH to 4.2, 4.7, 5.0, 5.8, or 6.3, the Ss was killed and the residual titer ratio was 90% or more at a heating temperature of 40 to 45° C. On the other hand, in the case where the heating treatment was performed without performing the pH adjustment (pH 3.1), the Ss was killed at a heating temperature of 40° C., and the residual titer ratio at 40° C. was 90% or more, but the value thereof was 92.2%, and therefore, the residual titer ratio was lower as compared with the case where the pH adjustment was performed. Further, the residual titer ratio was lower than 80% when the heating temperature was 45° C., and therefore, it was presumed that the temperature conditions in which the microorganism can be killed and the enzyme titer can be maintained are narrower by 5° C. or more as compared with the other pH conditions.

(3) Killing of Microorganism <Detailed Examination of Heating Temperature>

The pH of an Ss concentrate liquid (solid content: 5.6%) obtained in the same manner as in the above (1) was adjusted to 4.0, 4.5, 4.9, 5.7, or 6.5 with a 5 N sodium hydroxide solution. The thus obtained liquids were subjected to a heating treatment by maintaining the liquids at 44° C., 46° C., 48° C., 50° C., or 52° C. for 5 hours or 18 hours. The results of the live cell count of Ss before and after the heating treatment and the residual titer ratio are shown in Table 2 (5-hour heating treatment) and Table 3 (18-hour heating treatment).

heating treatment was performed after adjusting the pH to 4.5, the Ss was killed at a heating temperature of 46 to 50° C., and the residual titer ratio was 80% or more at 50° C., and 90% or more at 46 to 48° C. In the case where the heating treatment was performed after adjusting the pH to 4.9 or 5.7, the Ss was killed and the residual titer ratio was 90% or more at a heating temperature of 44 to 50° C. In particular, at a heating temperature of 46 to 50° C., the live cell count of Ss was 10 cfu/mL or less. In the case where the heating treatment was performed after adjusting the pH to 6.5, the Ss was killed at a heating temperature of 44 to 48° C., and the residual titer ratio was 80% or more at 48° C., and 90% or more at 44 to 46° C. In particular, at a heating temperature of 46 to 48° C., the live cell count of Ss was 10 cfu/mL.

Further, in the 18-hour heating treatment, in the case where the heating treatment was performed after adjusting the pH to 4.0, the Ss was killed at a heating temperature of 44 to 46° C., and the residual titer ratio was 80% or more at 46° C., and 90% or more at 44° C. In the case where the heating treatment was performed after adjusting the pH to 4.5, 4.9, or 5.7, the Ss was killed at a heating temperature of 44 to 48° C., and the residual titer ratio was 80% or more at 48° C., and 90% or more at 44 to 46° C. In the case where the heating treatment was performed after adjusting the pH to 6.5, the Ss was killed and the residual titer ratio was 90% or more at a heating temperature of 44 to 46° C.

(4) Killing of Microorganism <Examination of Heating Time>

The pH of an Ss concentrate liquid (solid content: 5.0%) obtained in the same manner as in the above (1) was adjusted

TABLE 2

| | Before heating | 44° C. | | 46° C. | | 48° C. | | 50° C. | | 52° C. | |
|---|---|---|---|---|---|---|---|---|---|---|---|
| | Live cell count (cfu/mL) | Residual titer ratio (%) | Live cell count (cfu/mL) | Residual titer ratio (%) | Live cell count (cfu/mL) | Residual titer ratio (%) | Live cell count (cfu/mL) | Residual titer ratio (%) | Live cell count (cfu/mL) | Residual titer ratio (%) | Live cell count (cfu/mL) |
| pH 4.0 | 3.9E+10 | 95.1 | <10 | 95.6 | <10 | 87.4 | <10 | 67.3 | <10 | 37.2 | <10 |
| pH 4.5 | 7.0E+09 | — | — | 100.6 | <10 | 95.8 | <10 | 88.0 | <10 | — | — |
| pH 4.9 | 2.7E+11 | 98.8 | 1.7E+02 | 99.7 | <10 | 95.1 | <10 | 91.8 | <10 | 60.3 | <10 |
| pH 5.7 | 2.2E+10 | 99.7 | 4.5E+02 | 97.6 | <10 | 92.1 | <10 | 94.1 | <10 | 55.8 | <10 |
| pH 6.5 | 1.1E+10 | 99.1 | 2.4E+03 | 93.9 | <10 | 87.5 | <10 | 73.1 | <10 | 44.9 | <10 |

TABLE 3

| | Before heating | 44° C. | | 46° C. | | 48° C. | | 50° C. | |
|---|---|---|---|---|---|---|---|---|---|
| | Live cell count (cfu/mL) | Residual titer ratio (%) | Live cell count (cfu/mL) | Residual titer ratio (%) | Live cell count (cfu/mL) | Residual titer ratio (%) | Live cell count (cfu/mL) | Residual titer ratio (%) | Live cell count (cfu/mL) |
| pH 4.0 | 3.9E+10 | 94.5 | <10 | 87.3 | <10 | 70.0 | <10 | 46.3 | <10 |
| pH 4.5 | 7.0E+09 | — | — | 91.0 | <10 | 80.3 | <10 | 65.5 | <10 |
| pH 4.9 | 2.7E+11 | 100.3 | <10 | 96.1 | <10 | 84.5 | <10 | 72.3 | <10 |
| pH 5.7 | 2.2E+10 | 96.9 | <10 | 101.4 | <10 | 81.6 | <10 | 76.9 | <10 |
| pH 6.5 | 1.1E+10 | 96.7 | <10 | 94.0 | <10 | 77.0 | <10 | 57.6 | <10 |

In the 5-hour heating treatment, in the case where the heating treatment was performed after adjusting the pH to 4.0, the Ss was killed at a heating temperature of 44 to 48° C., and the residual titer ratio was 80% or more at 48° C., and 90% or more at 44 to 46° C. In the case where the to 4.5 with a 5 N sodium hydroxide solution. The thus obtained liquid was subjected to a heat treatment by maintaining the liquid at 40° C. or 45° C. The results of the live cell count of Ss measured over time during the heating treatment are shown in Table 4.

TABLE 4

| Maintaining time (hour) | Heating temperature | |
|---|---|---|
| | 40° C. | 45° C. |
| 0 | 1.3E+09 | 3.0E+09 |
| 1 | 1.5E+08 | 5.0E+01 |
| 2 | 9.0E+06 | <10 |
| 3 | 2.2E+06 | <10 |
| 4 | 9.0E+04 | <10 |
| 5 | 6.0E+03 | <10 |
| 6 | 1.7E+02 | <10 |
| 9 | <10 | <10 |
| 13 | <10 | <10 |
| 18 | <10 | <10 |

The live cell count of Ss was decreased over time at either of the heating temperatures of 40° C. and 45° C., and in the case where the heating treatment was performed at 40° C., the live cell count was decreased to 1000 cfu/mL or less when performing the heating treatment for 6 hours, and decreased to 10 cfu/mL or less when performing the heating treatment for 9 hours. Further, in the case where the heating treatment was performed at 45° C., the live cell count was decreased to 1000 cfu/mL or less when performing the heating treatment for 1 hour, and decreased to 10 cfu/mL or less when performing the heating treatment for 2 hours.

(5) Killing of Microorganism <in Combination with Lactose>

By using an Ss concentrate liquid (solid content: 5.6%) obtained in the same manner as in the above (1), three types of samples were prepared as follows: a sample in which the pH of the Ss concentrate liquid was adjusted to 4.5 with a 5 N sodium hydroxide solution; a sample in which lactose was added at 1% to the Ss concentrate liquid (the pH adjustment was not performed); and a sample in which lactose was added at 1% to the Ss concentrate liquid, and then, the pH thereof was adjusted to 4.5. The thus obtained samples were subjected to a heating treatment by maintaining the samples at 50° C. for 18 hours (test I). Another test was performed in the same manner as described above for the case where lactose was added at 2% (test II). The residual titer ratio of each of the Ss suspensions is shown in Table 5. Incidentally, the live cell count of Ss after the heating treatment was 10 cfu/mL or less in all the cases.

TABLE 5

| | Only pH adjustment | Only addition of lactose | pH adjustment + addition of lactose |
|---|---|---|---|
| Test I | 61.8 | 72.0 | 87.9 |
| Test II | 62.9 | 84.3 | 94.4 |

In both the tests I and II, the residual titer ratio in the case where the pH adjustment and the addition of lactose were combined was higher than that in the case where a single treatment of either of the pH adjustment and the addition of lactose was performed. It was found that an effect of stabilizing the titer by the pH adjustment was exhibited even in the presence of lactose, and moreover, the residual titer ratio was increased in the presence of lactose.

Example 2

Preparation of Dry Product:

The pH of an Ss concentrate liquid (solid content: 5.3%) obtained in the same manner as in Example 1 was adjusted to 4.5 with a 5 N sodium hydroxide solution. The thus obtained liquid was subjected to a heating treatment by maintaining the liquid at 40° C. for 18 hours. To 7.8 L of this killed Ss concentrate liquid, 2.6 L of a 8, 20, or 40% lactose solution was added, followed by mixing well, whereby stock solutions to be dried were prepared such that the solid content of Ss was about 4%, and the lactose content was 2, 5, or 10%. These stock solutions and the killed Ss concentrate liquid to which lactose was not added were dried using a pilot apparatus for spray drying (PRODUCTION MINOR, GEA Process Engineering, Inc.) under conditions that the inlet temperature was 120° C., the outlet temperature was about 80° C., the rotation speed of the atomizer was 12500 rpm, and the processing amount of the stock solution was 4 kg/hr, whereby favorable dry products were obtained. The measurement results of the residual titer ratio (the ratio of the titer per solid content in the dry product to the titer per solid content in the stock solution to be dried), the average particle size, and the residual water content of each of these dry products are shown in Table 6.

TABLE 6

| | | Product 1 | Product 2 | Product 3 | Product 4 |
|---|---|---|---|---|---|
| Concentration in stock solution to be dried (%) | Ss | 4 | 4 | 4 | 4 |
| | Lactose | 2 | 5 | 10 | 0 |
| | Total solid content | 6 | 9 | 14 | 4 |
| Rotation speed of atomizer (rpm) | | 12500 | 12500 | 12500 | 12500 |
| Feeding amount of stock solution (kg/hr) | | 4.0 | 4.0 | 4.0 | 4.0 |
| Inlet temperature of drying chamber (° C.) | | 120 | 120 | 120 | 120 |
| Outlet temperature of drying chamber (° C.) | | 80 | 80 | 80 | 80 |
| Dry product | Average particle size (μm) | 19.6 | 21.5 | 24.5 | 18.3 |
| | Residual water content (%) | 4.7 | 4.6 | 5.2 | 4.9 |
| | Residual titer ratio (%) | 92.1 | 96.9 | 99.8 | 97.8 |

In the case where the concentration of lactose in the stock solutions to be dried was from 0 to 10%, dry products in which the residual titer ratio after drying was 90% or more could be obtained. Incidentally, the live cell count of Ss in any of these dry products was 10 cfu/mL or less, and the residual titer ratio before and after the heating treatment was 90% or more in all the cases.

Example 3

Test for Production of Oligosaccharides:

(1) Preparation of Suspension of Dry Product

Among the dry products obtained in the above-described Example 2, each of Product 1 and Product 2 in an amount corresponding to 45 U was weighed, and 10 mL of ion exchanged water was added thereto to suspend the dry product.

(2) Production Reaction of Oligosaccharides

To 800 mL of a 60% lactose solution, the entire amount of each of the suspensions of the dry products prepared in the above (1) or an Ss concentrate liquid obtained in the same manner as in Example 1 in an amount corresponding to 45 U was added and mixed, and a reaction was allowed to proceed at 65° C. for 22 hours at pH 6. The results obtained by examining the sugar composition at this time are shown in Table 7.

TABLE 7

| | | Product 1 | Product 2 | Ss concentrate liquid |
|---|---|---|---|---|
| Sugar composition (%) | Tetra- or higher oligosaccharide | 1.0 | 1.0 | 0.9 |
| | Trisaccharide | 30.1 | 30.0 | 29.6 |
| | Disaccharide | 57.8 | 58.0 | 58.7 |
| | Glc | 10.8 | 10.7 | 10.5 |
| | Gal | 0.3 | 0.3 | 0.4 |

There is no significant difference in sugar composition to be produced or reaction rate between each of the suspensions of the dry products and the Ss concentrate liquid (live cell suspension), and it was found that the dry product can be used in the production of oligosaccharides.

Example 4

Killing of Microorganism:
(1) Culturing
An Ss concentrate liquid (solid content: 5.8%) was obtained in the same manner as in (1) of Example 1.

(2) Killing of Microorganism <Examination of Concentration of Lactose and Heating Temperature>
The Ss concentrate liquid obtained in the above (1) and a lactose solution were mixed at 3:1, whereby Ss concentrate liquids containing lactose at 0.2 to 15% were prepared. The thus obtained liquids and the Ss concentrate liquid to which lactose was not added were subjected to a heating treatment by maintaining the liquids at 35° C., 40° C., 45° C., 50° C., or 55° C. for 18 hours. The results of the measurement of the live cell count of Ss before and after the heating treatment and the ratio of the β-galactosidase titer after the heating treatment to the β-galactosidase titer before the heating treatment (residual titer ratio) are shown in Table 8.

In the case where the heating treatment was performed after adding lactose at 0.2%, the Ss was killed at a heating temperature of 40 to 45° C., and the residual titer ratio was 80% or more at 45° C., and 90% or more at 40° C. In the case where the heating treatment was performed after adding lactose at 0.5 to 1%, the Ss was killed at 40 to 45° C., and the residual titer ratio was 90% or more. In the case where the heating treatment was performed after adding lactose at 2 to 5%, the Ss was killed and the residual titer ratio was 90% or more at a heating temperature of 40 to 50° C. In the case where the heating treatment was performed after adding lactose at 10 to 15%, the Ss was killed and the residual titer ratio was 90% or more at a heating temperature of 40 to 55° C. On the other hand, in the case where the heating treatment was performed without adding lactose, the Ss was killed at a heating temperature of 40° C., and the residual titer ratio at 40° C. was 90% or more, but the residual titer ratio was lower than 80% at 45° C., and therefore, it was presumed that the temperature conditions in which the microorganism can be killed and the enzyme titer can be maintained are narrower by 5° C. or more as compared with the case where lactose is added.

(3) Killing of Microorganism <Examination of Type of Carbohydrate>
An effect of stabilizing the enzymatic activity when a microorganism was killed was compared among a dextrin (NSD #300, San-ei Sucrochemical Co., Ltd.), a tri- or higher oligosaccharide fraction of a galactooligosaccharide, lactose, maltose, and glucose. An Ss concentrate liquid (solid content: 5.6%) obtained in the same manner as in the above (1) and a 8 or 20% carbohydrate solution were mixed at 3:1, whereby Ss concentrate liquids containing a carbohydrate at 2% or 5% were prepared. The thus obtained liquids were subjected to a heating treatment by maintaining the liquids at 45° C. or 50° C. for 18 hours. The results of the ratio of the β-galactosidase titer after the heating treatment to the β-galactosidase titer before the heating treatment (residual titer ratio) are shown in Table 9. The live cell count of Ss before the heating treatment was $10^8$ cfu/mL, however, after the heating treatment, the live cell count of Ss was decreased to 10 cfu/mL or less, and therefore, the Ss was killed in the case of any carbohydrate at any concentration.

TABLE 8

| | | Before heating | 35° C. | | 40° C. | | 45° C. | | 50° C. | | 55° C. | |
|---|---|---|---|---|---|---|---|---|---|---|---|---|
| | | Live cell count (cfu/mL) | Residual titer ratio (%) | Live cell count (cfu/mL) | Residual titer ratio (%) | Live cell count (cfu/mL) | Residual titer ratio (%) | Live cell count (cfu/mL) | Residual titer ratio (%) | Live cell count (cfu/mL) | Residual titer ratio (%) | Live cell count (cfu/mL) |
| Concentration of lactose (w/v) | 0% (without addition) | 1.7E+10 | 98.3 | 6.0E+07 | 97.0 | 4.0E+01 | 73.8 | <10 | 28.2 | <10 | — | — |
| | 0.2% | 7.0E+09 | 101.3 | 4.0E+07 | 101.3 | <10 | 81.8 | <10 | 37.6 | <10 | — | — |
| | 0.5% | 9.0E+09 | 101.6 | 8.0E+07 | 103.1 | <10 | 92.1 | <10 | 55.4 | <10 | — | — |
| | 1% | 1.3E+10 | 101.5 | 1.3E+08 | 100.0 | <10 | 100.8 | <10 | 75.9 | <10 | — | — |
| | 2% | 1.3E+10 | 99.7 | 3.0E+07 | 105.3 | <10 | 106.7 | <10 | 90.7 | <10 | — | — |
| | 5% | 1.0E+10 | — | — | 105.8 | <10 | 105.0 | <10 | 101.5 | <10 | 60.4 | <10 |
| | 10% | 1.4E+10 | — | — | 105.4 | <10 | 103.7 | <10 | 103.0 | <10 | 92.7 | <10 |
| | 15% | 7.0E+10 | — | — | 104.4 | <10 | 104.5 | <10 | 102.2 | <10 | 98.5 | <10 |

—: not tested

TABLE 9

|  |  | Concentration of carbohydrate (w/v) and heating temperature | | | |
|---|---|---|---|---|---|
|  |  | 2% | | 5% | |
|  |  | 45° C. | 50° C. | 45° C. | 50° C. |
| Type of carbohydrate | Dextrin NSD 300 | 93.9 | 48.6 | 98.8 | 68.8 |
|  | Tri- or higher oligosaccharide fraction of galactooligosaccharide | 102.5 | 81.5 | 108.1 | 97.8 |
|  | Lactose | 103.5 | 83.4 | 103.6 | 101.1 |
|  | Maltose | 101.3 | 91.0 | 104.8 | 98.2 |
|  | Glucose | 104.4 | 88.5 | 107.3 | 99.4 |

In the case where the carbohydrate was not added, the residual titer ratio was 72.7% at a heating temperature of 45° C., and 29.5% at a heating temperature of 50° C. On the other hand, in the case where any of the carbohydrates was allowed to coexist, the residual titer ratio was higher, and except the case where the dextrin was allowed to coexist at a heating temperature of 50° C., the residual titer ratio was improved to 80% or more.

(4) Killing of Microorganism <Examination of Heating Temperature>

An Ss concentrate liquid (solid content: 5.0%) obtained in the same manner as in the above (1) and a 20% lactose solution were mixed at 3:1, whereby an Ss concentrate liquid containing lactose at 5% was prepared. The thus obtained liquid was subjected to a heating treatment by maintaining the liquid at 40° C. or 45° C. The results of the live cell count of Ss measured over time during the heating treatment are shown in Table 10.

TABLE 10

| Maintaining time (hour) | Heating temperature | |
|---|---|---|
|  | 40° C. | 45° C. |
| 0 | 1.7E+09 | 3.0E+09 |
| 1 | 1.1E+07 | <10 |
| 2 | 9.0E+04 | <10 |
| 3 | 6.0E+03 | <10 |
| 4 | 2.1E+01 | <10 |
| 5 | <10 | <10 |
| 6 | <10 | <10 |
| 9 | <10 | <10 |
| 13 | <10 | <10 |
| 18 | <10 | <10 |

The live cell count of Ss was decreased over time at either of the heating temperatures of 40° C. and 45° C., and in the case where the heating treatment was performed at 40° C., the live cell count was decreased to 1000 cfu/mL or less when performing the heating treatment for 4 hours, and decreased to 10 cfu/mL or less when performing the heating treatment for 5 hours. Further, in the case where the heating treatment was performed at 45° C., the live cell count was decreased to 10 cfu/mL or less when performing the heating treatment for 1 hour.

(5) Killing of Microorganism <Examination of Sugar Composition>

An Ss concentrate liquid (solid content: 5.3%) obtained in the same manner as in the above (1) and a 8, 20, or 40% lactose solution were mixed at 3:1, whereby Ss concentrate liquids containing lactose at 2%, 5%, or 10% were prepared. The thus obtained liquids were subjected to a heating treatment by maintaining the liquids at 40° C. for 18 hours. The sugar composition after the heating treatment was analyzed under the above HPLC conditions. The results are shown in Table 11. Further, the results obtained by measuring the titer before the heating treatment and calculating a residual titer are also shown in Table 11. The live cell count of Ss before the heating treatment was $10^8$ cfu/mL, however, after the heating treatment, the live cell count of Ss was decreased to 10 cfu/mL or less, and therefore, the Ss was killed in all the cases.

TABLE 11

| Concentration of lactose (w/v) | Sugar composition (%) | | | Residual titer ratio (%) |
|---|---|---|---|---|
|  | Tri- or higher oligosaccharide | Disaccharide | Monosaccharide |  |
| 2% | 0.0 | 5.3 | 94.7 | 104.1 |
| 5% | 0.2 | 12.4 | 87.4 | 105.6 |
| 10% | 6.1 | 42.7 | 51.3 | 104.4 |

In the Ss concentrate liquid (live cell suspension) containing lactose, lactose is subjected to the β-galactosidase activity during the heating treatment, however, it was found that the effect of stabilizing the titer is maintained regardless of the degree of the reaction. Further, it was confirmed that even if a monosaccharide (glucose or galactose) or a galactooligosaccharide produced by subjecting the added lactose to an enzymatic reaction exists in the Ss concentrate liquid, there is no problem in terms of stabilization of the enzyme titer, and it was also confirmed that a monosaccharide or a galactooligosaccharide can be used as the carbohydrate.

Example 5

Preparation of Dry Product:

An Ss concentrate liquid (solid content: 5.3%) obtained in the same manner as in Example 1 and a 8, 20, or 40% lactose solution were mixed at 3:1, whereby stock solutions to be dried were prepared such that the solid content of Ss was about 4%, and the lactose content was 2, 5, or 10%. The thus obtained liquids were subjected to a heating treatment by maintaining the liquids at 40° C. for 18 hours. These killed Ss concentrate liquids were dried using a pilot apparatus for spray drying (PRODUCTION MINOR, GEA Process Engineering, Inc.) under conditions that the inlet temperature was 120° C., the outlet temperature was about 80° C., the rotation speed of the atomizer was 12500 rpm, and the processing amount of the stock solution was 4 kg/hr, whereby favorable dry products were obtained. The residual titer ratio (the ratio of the titer per solid content in the dry product to the titer per solid content in the stock solution to be dried), the average particle size, and the residual water content of each of these dry products were measured. The results are shown in Table 12.

TABLE 12

|  |  | Product 5 | Product 6 | Product 7 |
|---|---|---|---|---|
| Concentration in stock solution to be dried (%) | Ss | 4 | 4 | 4 |
|  | Lactose | 2 | 5 | 10 |
|  | Total solid content | 6 | 9 | 14 |
| Rotation speed of atomizer (rpm) | | 12500 | 12500 | 12500 |
| Feeding amount of stock solution (kg/hr) | | 4.0 | 4.0 | 4.0 |
| Inlet temperature of drying chamber (° C.) | | 120 | 120 | 120 |
| Outlet temperature of drying chamber (° C.) | | 80 | 80 | 80 |
| Dry product | Average particle size (μm) | 22.9 | 22.4 | 26.8 |
|  | Residual water content (%) | 7.4 | 7.5 | 5.6 |
|  | Residual titer ratio (%) | 94.0 | 96.0 | 97.2 |

In the case where the concentration of lactose in the stock solutions to be dried was from 2 to 10%, dry microbial cell products in which the residual titer ratio after drying was 90% or more could be obtained. Incidentally, the live cell count of Ss in any of these dry products was 10 cfu/mL or less, and the residual titer ratio before and after the heating treatment was 90% or more in all the cases.

Example 6

Test for Production of Oligosaccharides:
(1) Preparation of Suspension of Dry Product Among the dry products obtained in the above-described Example 5, each of Product 5 and Product 6 in an amount corresponding to 45 U was weighed, and 10 mL of ion exchanged water was added thereto to suspend the dry product.

(2) Production Reaction of Oligosaccharides

To 800 mL of a 60% lactose solution, the entire amount of each of the suspensions of the dry products prepared in the above (1) or an Ss concentrate liquid obtained in the same manner as in Example 1 in an amount corresponding to 45 U was added and mixed, and a reaction was allowed to proceed at 65° C. for 22 hours at pH 6. The results obtained by examining the sugar composition at this time are shown in Table 13.

TABLE 13

|  |  | Product 5 | Product 6 | Ss concentrate liquid |
|---|---|---|---|---|
| Sugar composition (%) | Tetra- or higher oligosaccharide | 1.0 | 1.0 | 0.9 |
|  | Trisaccharide | 30.3 | 30.3 | 29.6 |
|  | Disaccharide | 57.2 | 57.4 | 58.7 |
|  | Glc | 11.0 | 11.0 | 10.5 |
|  | Gal | 0.4 | 0.4 | 0.4 |

There is no significant difference in sugar composition to be produced between each of the suspensions of the dry products and the Ss concentrate liquid (live cell suspension), and it was found that the dry product can be used in the production of oligosaccharides.

Example 7

Killing of Microorganism:
(1) Culturing

An Ss concentrate liquid (solid content: 5.2%) was obtained in the same manner as in (1) of Example 1.

(2) Killing of Microorganism <Examination of Concentration of Lactose and Heating Temperature>

The Ss concentrate liquid obtained in the above (1) and a lactose solution were mixed at 3:1, whereby Ss concentrate liquids containing lactose at 2 to 5% were prepared. The thus obtained liquids and the Ss concentrate liquid to which lactose was not added were subjected to a heating treatment by maintaining the liquids at 50° C. for 18 hours. The results of the ratio of the β-galactosidase titer after the heating treatment to the β-galactosidase titer before the heating treatment (residual titer ratio) are shown in Table 14. Incidentally, the live cell count of Ss after the heating treatment was 10 cfu/mL or less in all the cases.

TABLE 14

| Concentration of lactose (w/v) | Residual titer ratio (%) |
|---|---|
| 2% | 85.2 |
| 3% | 95.8 |
| 4% | 98.2 |
| 5% | 102.0 |

The residual titer ratio was higher than 80% in the case where the concentration of lactose was from 2 to 5%. Further, it was found that in the case where the concentration of lactose was 3% or more, the residual titer ratio was higher than 90%.

Example 8

Killing of Microorganism:
(1) Culturing

An Ss concentrate liquid (solid content: 5.4%) was obtained in the same manner as in (1) of Example 1.

(2) Killing of Microorganism <in Combination with Lactose>

By using the Ss concentrate liquid obtained in the above (1), three types of samples were prepared as follows: a sample in which the pH of the Ss concentrate liquid was adjusted to 4.5 with a 2 N sodium hydroxide solution; a sample in which lactose was added at 1% to the Ss concentrate liquid (the pH adjustment was not performed); and a sample in which lactose was added at 1% to the Ss concentrate liquid, and then, the pH thereof was adjusted to 4.5. The thus obtained samples were subjected to a heating treatment by maintaining the samples at 45° C. for 18 hours (test III). Another test was performed in the same manner as described above for the case where lactose was added at 2% (test IV). The residual titer ratio of each of the Ss suspensions is shown in Table 15. The live cell count of Ss after the heating treatment was 10 cfu/mL or less in all the cases.

TABLE 15

|  | Only pH adjustment | Only addition of lactose | pH adjustment + addition of lactose |
|---|---|---|---|
| Test III | 97.2 | 100.2 | 102.9 |
| Test IV | 98.3 | 102.0 | 103.1 |

In both the tests III and IV, the residual titer ratio in the case where the pH adjustment and the addition of lactose were combined was higher than that in the case where a single treatment of either of the pH adjustment and the addition of lactose was performed. It was found that an effect of stabilizing the titer by the pH adjustment was exhibited even in the presence of lactose, and moreover, the residual titer ratio was increased in the presence of lactose.

(3) Killing of Microorganism <in Combination with Lactose>

By using the Ss concentrate liquid obtained in the above (1), three types of samples were prepared as follows: a sample in which the pH of the Ss concentrate liquid was adjusted to 4.5, 5.0, or 5.5 with a 2 N sodium hydroxide solution; a sample in which lactose was added at 2% to the Ss concentrate liquid (the pH adjustment was not performed); and a sample in which lactose was added at 2% to the Ss concentrate liquid, and then, the pH thereof was adjusted to 4.5, 5.0, or 5.5. The thus obtained samples were subjected to a heating treatment by maintaining the samples at 50° C. for 5 hours or 18 hours. The residual titer ratio of each of the Ss suspensions is shown in Table 16. Incidentally, the live cell count of Ss after the heating treatment was 10 cfu/mL or less in all the cases.

TABLE 16

| | | 50° C. | | | |
|---|---|---|---|---|---|
| | | Maintaining time 5 hr | | Maintaining time 18 hr | |
| Treatment conditions | Live cell count before heating (cfu/ml) | Residual titer ratio (%) | Live cell count (cfu/ml) | Residual titer ratio (%) | Live cell count (cfu/ml) |
| 2% lactose | 9.2E+10 | 100.1 | <10 | 89.7 | <10 |
| pH 4.5 | 4.6E+10 | 88.0 | <10 | 65.5 | <10 |
| pH 4.5 + 2% lactose | 7.3E+10 | 102.9 | <10 | 97.1 | <10 |
| pH 5.0 | 1.1E+11 | 91.8 | <10 | 72.3 | <10 |
| pH 5.0 + 2% lactose | 1.0E+11 | 103.6 | <10 | 99.5 | <10 |
| pH 5.5 | 6.1E+09 | 94.1 | <10 | 76.9 | <10 |
| pH 5.5 + 2% lactose | 4.6E+10 | 100.8 | <10 | 99.5 | <10 |

In all the cases, the residual titer ratio in the case where the pH adjustment and the addition of lactose were combined was higher than that in the case where a single treatment of either of the pH adjustment and the addition of lactose was performed. Further, in the case where the heating maintaining time was 18 hours, by adjusting the pH to 4.5 to 5.5, the residual titer ratio was 90% or more even when the concentration of lactose was 2%.

Example 9

Killing of Microorganism:
(1) Culturing

Ss was aerobically cultured at 27° C. for 4 days in a medium (pH 5) containing glucose (2%), yeast extract (0.4%), monopotassium phosphate (0.05%), and magnesium sulfate (0.025%). This culture solution was centrifuged (10000 G, 30 min) to obtain wet cells, and sterilized tap water was added thereto and the wet cells were well suspended therein. The resulting suspension was centrifuged under the same conditions, and to the obtained wet cells, a lactose solution and sterilized water were added, whereby Ss concentrate liquids containing lactose at 2% or 5% and having a cell density of 2.5%, 4.5%, or 6.5% (w/v) were prepared.

(2) Killing of Microorganism <Examination of Concentration of Lactose and Heating Temperature>

The Ss concentrate liquids obtained in the above (1) were subjected to a heating treatment by maintaining the liquids at 45° C. or 50° C. for 5 hours or 18 hours. The measurement of the live cell count of Ss before and after the heating treatment and the ratio of the β-galactosidase titer after the heating treatment to the β-galactosidase titer before the heating treatment (residual titer ratio) are shown in FIGS. 1 to 4.

At any cell density, the residual titer ratio after killing the microorganism was 80% or more, and a difference in residual titer ratio was not observed. In particular, in the case where the concentration of lactose was 5%, the residual titer ratio after killing the microorganism was 90% or more at any cell density.

Example 10

Killing of Microorganism:
(1) Culturing

Ss was aerobically cultured at 27° C. for 4 days in a medium (pH 5) containing glucose (4%), yeast extract (0.8%), monopotassium phosphate (0.1%), and magnesium sulfate (0.05%), whereby an Ss culture solution (solid content: 2.5%) was obtained.

(2) Killing of Microorganism

The pH of the Ss culture solution obtained in the above (1) was adjusted stepwise from 3.5 to 5.0 with a 2 N sodium hydroxide solution. The thus obtained solutions and the Ss culture solution in which the pH adjustment was not performed were subjected to a heating treatment by maintaining the solutions at 40° C. or 45° C. for 5 hours or 18 hours. The results of the live cell count of Ss after the heating treatment and the ratio of the β-galactosidase titer after the heating treatment to the β-galactosidase titer before the heating treatment (residual titer ratio) are shown in Table 17.

TABLE 17

| | | | | Culture lot No. | | | | | |
|---|---|---|---|---|---|---|---|---|---|
| | | | | Lot. 1 | | Lot. 2 | | Lot. 3 | |
| | | | | Titer after completion of culturing (U/g) | | | | | |
| | | | | 2.29 | | 2.52 | | 2.37 | |
| | | | | Unadjusted pH | | | | | |
| | | | | 3.10 | | 3.17 | | 3.53 | |
| | Conditions | | | Residual | Live cell | Residual | Live cell | Residual | Live cell |
| | pH | Temperature (° C.) | Time (h) | titer ratio (%) | count (cfu/ml) | titer ratio (%) | count (cfu/ml) | titer ratio (%) | count (cfu/ml) |
| Treatment of killing microorganism | Unadjusted | 40 | 5 | 65.9 | >1.0E+02 | — | — | 95.2 | 4.3E+04 |
| | | | 18 | 64.1 | <10 | — | — | 94.2 | <10 |
| | | 45 | 5 | 41.0 | <10 | — | — | 85.0 | <10 |
| | | | 18 | 31.3 | <10 | — | — | 77.9 | <10 |
| | 3.5 | 40 | 5 | — | — | 86.3 | 4.6E+04 | — | — |
| | | | 18 | — | — | 85.8 | <10 | — | — |
| | | 45 | 5 | — | — | 72.4 | <10 | — | — |
| | | | 18 | — | — | 64.0 | <10 | — | — |
| | 4.0 | 40 | 5 | 94.2 | >1.0E+02 | 95.0 | 4.6E+06 | 99.0 | 1.2E+06 |
| | | | 18 | 96.2 | <10 | 95.7 | <10 | 98.7 | 7.0E+00 |
| | | 45 | 5 | 92.9 | <10 | 90.0 | <10 | 98.5 | <10 |
| | | | 18 | 80.3 | <10 | 79.3 | <10 | 94.2 | <10 |

TABLE 17-continued

| | | | Culture lot No. | | | | | |
|---|---|---|---|---|---|---|---|---|
| | | | Lot. 1 | | Lot. 2 | | Lot. 3 | |
| | | | Titer after completion of culturing (U/g) | | | | | |
| | | | 2.29 | | 2.52 | | 2.37 | |
| | | | Unadjusted pH | | | | | |
| | | | 3.10 | | 3.17 | | 3.53 | |
| Conditions | | | Residual | Live cell | Residual | Live cell | Residual | Live cell |
| pH | Temperature (° C.) | Time (h) | titer ratio (%) | count (cfu/ml) | titer ratio (%) | count (cfu/ml) | titer ratio (%) | count (cfu/ml) |
| 4.5 | 40 | 5 | 95.4 | >1.0E+02 | 96.5 | 9.9E+06 | 99.7 | 2.0E+06 |
| | | 18 | 98.1 | <10 | 99.9 | <10 | 102.6 | <10 |
| | 45 | 5 | 96.9 | <10 | 98.3 | <10 | 99.8 | <10 |
| | | 18 | 88.4 | <10 | 91.9 | <10 | 99.7 | <10 |
| 5.0 | 40 | 5 | 95.4 | >1.0E+02 | 99.5 | 1.5E+07 | 100.3 | 1.5E+07 |
| | | 18 | 98.1 | <10 | 101.5 | <10 | 99.0 | 1.7E+02 |
| | 45 | 5 | 99.9 | <10 | 101.7 | <10 | 100.7 | <10 |
| | | 18 | 90.8 | <10 | 94.9 | <10 | 100.8 | <10 |

In any of the culture solutions, as the pH during the treatment of killing the microorganism was higher, the residual titer ratio was improved. Further, in any of the culture solutions, the conditions that met the requirements of 80% or more of the residual titer ratio and 10 cfu/mL or less of the live cell count of Ss were such that the pH was adjusted to 4.0 or higher and the heating treatment was performed at 45° C. for 5 hours. Further, also in the case where the pH was adjusted to 5.0 and the heating treatment was performed at 45° C. for 18 hours, the above-described requirement of the residual titer ratio was met.

Example 11

Figure 5:
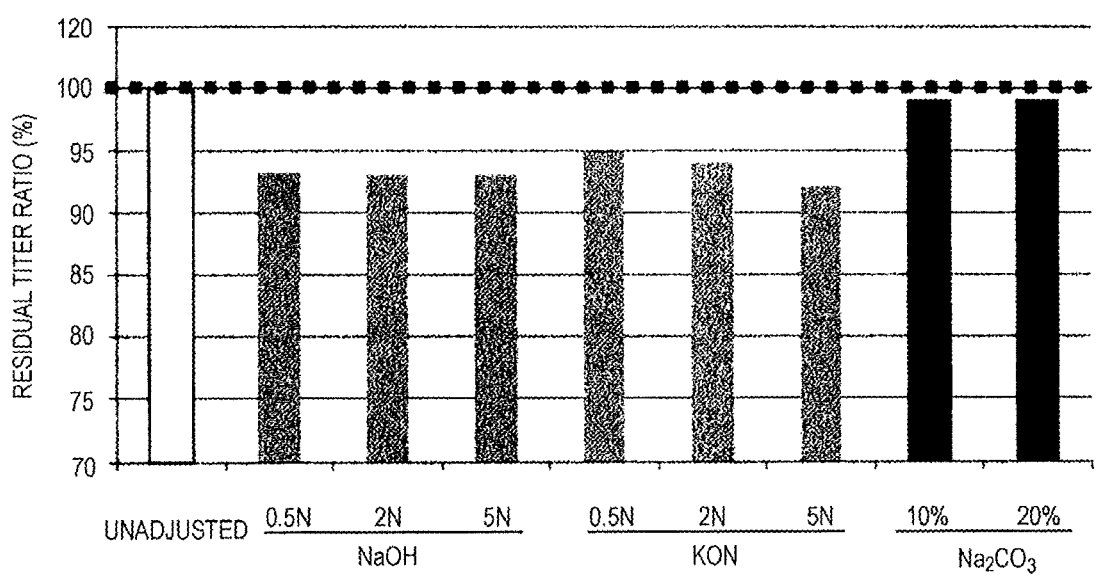
FIG. 5 is a view showing a residual titer ratio after adjusting the pH of an Ss culture solution using a sodium hydroxide solution, a potassium hydroxide solution, or a sodium carbonate solution at various concentrations in Example 11.

Examination of pH Adjusting Agent:
(1) Culturing
Ss was aerobically cultured at 27° C. for 4 days in a medium (pH 5) containing glucose (4%), yeast extract (0.8%), monopotassium phosphate (0.1%), and magnesium sulfate (0.05%), whereby an Ss culture solution (solid content: 2.8%) was obtained.
(2) pH Adjustment
To the Ss culture solution obtained in the above (1), a 0.5, 2, or 5 N sodium hydroxide solution or potassium hydroxide solution, or a 10 or 20% sodium carbonate solution was added dropwise, whereby the pH of the solution was adjusted to 5.0. The ratio of the β-galactosidase titer after the pH adjustment to the β-galactosidase titer before the pH adjustment (residual titer ratio) is shown in FIG. 5.

In the case where sodium hydroxide or sodium hydroxide was used as the pH adjusting agent, the titer was decreased by 7 to 8% immediately after the pH adjustment. On the other hand, in the case where sodium carbonate was used as the pH adjusting agent, the titer was hardly decreased.

Example 12

Examination of pH Adjusting Agent:
(1) Culturing
Ss was aerobically cultured at 27° C. for 4 days in a medium (pH 5) containing glucose (5%), yeast extract (1%), monopotassium phosphate (0.1%), and magnesium sulfate (0.050), whereby an Ss culture solution (solid content: 2.5%) was obtained.
(2) Killing of Microorganism
The pH of the Ss culture solution obtained in the above (1) was adjusted stepwise from 4.0 to 5.0 with a 2 N sodium hydroxide solution or a 20% sodium carbonate solution. The thus obtained solutions were subjected to a heating treatment by maintaining the solutions at 40° C. or 45° C. for 5 hours or 18 hours. The live cell count of Ss after the heating treatment and the ratio of the β-galactosidase titer after the heating treatment to the β-galactosidase titer before the heating treatment (residual titer ratio) are shown in Table 18.

TABLE 18

| | | | | pH adjusting agent when killing microorganism | | | |
|---|---|---|---|---|---|---|---|
| | | | | 2N NaOH | | 20% $Na_2CO_3$ | |
| Conditions | | | | Residual | Live cell | Residual | Live cell |
| | pH | Temperature (° C.) | Time (h) | titer ratio (%) | count (cfu/ml) | titer ratio (%) | count (cfu/ml) |
| Treatment of killing microorganism | 4.0 | 40 | 5 | 99.7 | 6.7E+06 | 99.7 | 4.1E+06 |
| | | | 18 | 100.9 | <10 | 101.2 | <10 |
| | | 45 | 5 | 94.7 | <10 | 95.9 | <10 |
| | | | 18 | 86.5 | <10 | 87.1 | <10 |
| | 4.5 | 40 | 5 | 99.7 | 9.3E+09 | 99.6 | 5.8E+06 |
| | | | 18 | 102.4 | >1.0E+02 | 101.7 | >1.0E+02 |

TABLE 18-continued

| | | | pH adjusting agent when killing microorganism | | | |
|---|---|---|---|---|---|---|
| | | | 2N NaOH | | 20% $Na_2CO_3$ | |
| | Conditions | | Residual | Live cell | Residual | Live cell |
| pH | Temperature (° C.) | Time (h) | titer ratio (%) | count (cfu/ml) | titer ratio (%) | count (cfu/ml) |
| | 45 | 5 | 100.4 | <10 | 99.8 | <10 |
| | | 18 | 94.6 | <10 | 93.5 | <10 |
| 5.0 | 40 | 5 | 101.6 | 9.2E+06 | 103.7 | 7.8E+06 |
| | | 18 | 103.1 | >1.0E+02 | 100.0 | >1.0E+02 |
| | 45 | 5 | 104.2 | <10 | 102.1 | <10 |
| | | 18 | 98.9 | <10 | 97.5 | <10 |

A difference was not observed between the pH adjusting agents in terms of the residual titer ratio before and after the treatment of killing the microorganism and the live cell count of Ss.

Example 13

Preparation of Dry Product:
(1) Preparation of Ss Concentrate Liquid

Ss was aerobically cultured at 27° C. for 4 days in a medium (pH 5) containing glucose (4%), yeast extract (0.8%), monopotassium phosphate (0.1%), and magnesium sulfate (0.05%). This culture solution was centrifuged (10000 G, 30 mins), and a cell concentrate liquid was collected. Then, the cells were washed by adding sterilized tap water to the cell concentrate liquid and well suspending the cells. The resulting suspension was centrifuged under the same conditions, and adjustment was performed such that the solid content was about 5%, and the thus obtained material was used as an Ss concentrate liquid (solid content: 5.10).

(2) Preparation of Ss Culture Solution

Ss was aerobically cultured at 27° C. for 4 days in a medium (pH 5) containing glucose (4%), yeast extract (0.8%), monopotassium phosphate (0.1%), and magnesium sulfate (0.05%), whereby an Ss culture solution was obtained.

(3) Killing of Microorganism in Ss Concentrate Liquid (pH Adjustment)

The pH of the Ss concentrate liquid obtained in the above (1) was adjusted to 4.8±0.2 with a 20% sodium carbonate solution. The thus obtained Ss concentrate liquid was subjected to a heating treatment by maintaining the liquid at 45° C. for 7 hours. The results of the live cell count of Ss after the heating treatment and the ratio of the β-galactosidase titer after the heating treatment to the β-galactosidase titer before the heating treatment (residual titer ratio) are shown in Table 19. Further, immediately before drying, the Ss concentrate liquid after killing the microorganism and a 24% lactose solution were mixed at 5:1, whereby a stock solution to be dried containing lactose at 4% was prepared.

(4) Killing of Microorganism in Ss Concentrate Liquid (Coexistence of Lactose)

The Ss concentrate liquid obtained in the above (1) and a 24% lactose solution were mixed at 5:1, whereby an Ss concentrate liquid containing lactose at 4% was prepared. The thus prepared Ss concentrate liquid was subjected to a heating treatment by maintaining the liquid at 50° C. for 7 hours. The results of the live cell count of Ss after the heating treatment and the ratio of the β-galactosidase titer after the heating treatment to the β-galactosidase titer before the heating treatment (residual titer ratio) are shown in Table 19. The Ss concentrate liquid after killing the microorganism was directly used as a stock solution to be dried.

(5) Killing of Microorganism in Ss Concentrate Liquid (Combination of pH Adjustment and Coexistence of Lactose)

The Ss concentrate liquid obtained in the above (1) and a 24% lactose solution were mixed at 10:1, whereby an Ss concentrate liquid containing lactose at 2.2% was prepared. Further, the pH of the thus prepared Ss concentrate liquid was adjusted to 4.8±0.2 with a 20% sodium carbonate solution. The thus obtained Ss concentrate liquid was subjected to a heating treatment by maintaining the liquid at 50° C. for 7 hours. The results of the live cell count of Ss after the heating treatment and the ratio of the β-galactosidase titer after the heating treatment to the β-galactosidase titer before the heating treatment (residual titer ratio) are shown in Table 19. Further, immediately before drying, the Ss concentrate liquid after killing the microorganism and a 24% lactose solution were mixed at 11:1, whereby a stock solution to be dried containing lactose at 4% was prepared.

(6) Killing of Microorganism in Ss Concentrate Liquid (pH Adjustment)

The pH of the Ss culture solution obtained in the above (2) was adjusted to 4.8±0.2 with a 20% sodium carbonate solution. The thus obtained Ss culture solution was subjected to a heating treatment by maintaining the solution at 45° C. for 7 hours. The results of the live cell count of Ss after the heating treatment and the ratio of the β-galactosidase titer after the heating treatment to the β-galactosidase titer before the heating treatment (residual titer ratio) are shown in Table 19. Further, the Ss culture solution after killing the microorganism was centrifuged (16000 G), and wet cells were collected. Then, sterilized tap water was added thereto and the wet cells were well suspended therein and adjusted such that the solid content was about 5%, whereby an Ss concentrate liquid in which the microorganism was killed (solid content: 5.2%) was obtained. Immediately before drying, this Ss concentrate liquid in which the microorganism was killed and a 24% lactose solution were mixed at 5:1, whereby a stock solution to be dried containing lactose at 4% was prepared.

(7) Spray Drying

The stock solutions to be dried obtained in the above (3) to (6) were dried using a pilot apparatus for spray drying (PRODUCTION MINOR, GEA Process Engineering, Inc.) under conditions that the inlet temperature was 120° C., the outlet temperature was 80° C., the rotation speed of the atomizer was 15000 rpm, and the processing amount of the stock solution was about 4.5 kg/hr, whereby favorable dry products were obtained. The residual titer ratio, the average particle size, and the residual water content of each of these dry products were measured. The results are shown in Table 19.

5356 (ATCC 24193) was used in place of Ss, and as a result, substantially the same results were obtained with respect to the residual titer ratio and the like. For example, the residual titer ratio when the heating treatment was performed at pH 5.0 and 45° C. was 80% or more.

TABLE 19

|  |  |  | a | b | c | d |
|---|---|---|---|---|---|---|
| Stock solution |  |  | Concentrate liquid | | | Culture solution |
|  | Titer (U/kg) |  | 5500 | | | 2450 |
| Step of killing microorganism | Method for killing microorganism |  | pH adjusting method | Lactose coexistence method | pH/lactose combination method | pH adjusting method |
|  | Treatment conditions | Initial pH | 4.8 ± 0.2 | — | 4.8 ± 0.2 | 4.8 ± 0.2 |
|  |  | Concentration of lactose (%) | — | 4 | 2 | — |
|  |  | Temperature (° C.) | 45 | 50 | 50 | 45 |
|  |  | Maintaining time (hr) | 7 | 7 | 7 | 7 |
|  | pH (actual value) | Before killing microorganism | 4.9 | 3.9 | 5.0 | 4.7 |
|  |  | After killing microorganism | 5.1 | 4.7 | 5.2 | 4.7 |
|  | Liquid subjected to treatment of killing microorganism | Residual titer ratio (%) | 99.9 | 103.7 | 102.2 | 92.7 |
|  |  | Live cell count of Ss (cfu/mL) | <10 | <10 | <10 | <10 |
| Step of spray drying | Addition of stabilizing agent (lactose)/ additionally added amount (%) |  | 4 | — | 2 | 4 |
|  | Stock solution to be dried | Solid content concentration (w/v %) | Ss cells | 4.3 | 4.3 | 4.3 | 4.6 |
|  |  | Stabilizing agent (lactose) | 4 | 4 | 4 | 4 |
|  |  | Total solid content | 8.3 | 8.3 | 8.3 | 8.6 |
|  |  | Titer (U/kg) | 4680 | 4760 | 4720 | 4690 |
|  | Operating conditions | Rotation speed of atomizer (rpm) | | | 15000 | |
|  |  | Feeding amount of stock solution (kg/hr) | 4.5 | 4.5 | 4.4 | 4.6 |
|  |  | Temperature (° C.) Inlet | | | 120 | |
|  |  | Outlet | | | 80 | |
|  | Dry product | Average particle size (μm) | 21.1 | 18.4 | 19.5 | 20.0 |
|  |  | Residual water content (%) | 4.8 | 6.0 | 5.2 | 4.7 |
|  |  | Titer (U/g) | 54.2 | 49.7 | 52.6 | 55.0 |
|  |  | Residual titer ratio (%) | 96.2 | 91.3 | 95.3 | 95.8 |

In all the conditions for killing the microorganism, favorable dry products in which the residual titer ratio was 90% or more and the live cell count of Ss was less than 10 cfu/ml were obtained.

Example 14

Storage Test:

The dry products (Products 1 to 3) prepared in Example 2 and the dry products (Products 5 to 7) prepared in Example 5 were stored at 5° C. or 25° C. for 360 days. The ratio of the β-galactosidase titer after the storage to the β-galactosidase titer before the storage (residual titer ratio) was determined. The results are shown in Table 20.

TABLE 20

|  |  | Example 2 (pH adjustment) | | | Example 5 (addition of lactose) | | |
|---|---|---|---|---|---|---|---|
|  |  | Product 1 (lactose 2%) | Product 2 (lactose 5%) | Product 3 (lactose 10%) | Product 5 (lactose 2%) | Product 6 (lactose 5%) | Product 7 (lactose 10%) |
| Residual titer ratio (%) | 5° C. | 100.2 | 101.0 | 98.0 | 95.7 | 95.4 | 93.5 |
|  | 25° C. | 93.3 | 95.4 | 95.7 | 87.3 | 90.2 | 92.8 |

It was found that even if the dry products were stored at 5° C. or 25° C. for 360 days, the residual titer ratio was 80% or more.

Example 15

Killing of Microorganism:

A microorganism was killed in the same manner as in Example 1 except that *Sporobolomyces singularis* JCM Example 16

Killing of Microorganism <Examination of Sugar Composition>:

A microorganism was killed in the same manner as in Example 4 except that *Sporobolomyces singularis* JCM 5356 (ATCC 24193) was used in place of Ss, and as a result, substantially the same results were obtained with respect to the residual titer ratio and the like. For example, the residual titer ratio when the heating treatment was performed at a lactose concentration of 5% and 45° C. was 80% or more.

INDUSTRIAL APPLICABILITY

According to the present inventive method, a microorganism can be killed while maintaining the enzyme titer of a liquid of microbial cells having an enzymatic activity. Due to this, the microbial cell liquid treated by the present inventive method is easy to handle and also can be stored, and therefore can be advantageously used in the industry using the enzymatic activity.

The invention claimed is:

1. A method for killing a microorganism while maintaining an enzyme titer of a culture, the method comprising:
    culturing live microbial cells that produce said enzyme where the pH of the culture is adjusted to a pH to 4.5 to 5.7;
    adding maltose or glucose to the culture such that the culture comprises 2 mass/vol % or 5 mass/vol % of the maltose or glucose;
    wherein the culture does not comprise lactose; and
heating the culture containing 2 mass/vol % of glucose or 5 mass/vol % of maltose or glucose to 45° C. for 18 hours, or heating the culture containing 2 mass/vol % of maltose or glucose to 50° C. for 18 hours, such that the live microbial cells are killed and that a titer of the enzyme in the culture is maintained; and
    wherein the microbial cell is *Sporobolomyces singularis*.

2. The method of claim 1, wherein in the adjusting, the pH of the culture is adjusted to 4.7 to 5.0.

3. The method of claim 1, wherein the enzyme is β-galactosidase.

4. The method of claim 1, wherein the microbial cells are yeast cells.

5. The method of claim 1, wherein the titer of the enzyme after the heating is 80% or more compared to the titer of the enzyme before the heating.

6. The method of claim 1, wherein in the adjusting, the pH is adjusted by adding a carbonate to the culture.

7. The method of claim 1, wherein the heated culture comprises less than 10 cfu/mL of the live microbial cells.

8. The method of claim 1,
    wherein the pH of the culture is adjusted to 5.0, and
    the enzyme is β-galactosidase.

9. The method of claim 8, wherein, the culture containing 5 mass/vol % of glucose is heated to 45° C. for 18 hours, or the culture containing 2 mass/vol % of maltose or glucose is heated to 50° C. for 18 hours.

10. The method of claim 8, wherein, the culture containing 2 mass/vol % of maltose is heated to 50° C. for 18 hours.

* * * * *